United States Patent
Mitchell et al.

[11] Patent Number: 5,876,963
[45] Date of Patent: Mar. 2, 1999

[54] HUMAN NUCLEOTIDE PYROPHOSPHOHYDROLASE

[76] Inventors: Peter Mitchell, 5 Godfrey St., Mystic, Conn. 06355; Nancy Hutchinson, 7 Squire Hill, Old Lyme, Conn. 06371; Michael Lawton, 61 Magna Ln., Westbrook, Conn. 06498; Holly Magna, 88 Old Black Point Rd., Niantic, Conn. 06357; Sue Yocum, 11 Pinecrest Ln., Baltic, Conn. 06330; Lynn E. Murry, 1124 Los Trancos Rd., Portola Valley, Calif. 94028

[21] Appl. No.: 918,914

[22] Filed: Aug. 27, 1997

[51] Int. Cl.$^6$ .......................... C07H 21/04; C12N 15/63; C12N 15/85
[52] U.S. Cl. .................... 435/69.1; 536/23.5; 536/24.31; 536/24.3; 435/252.3; 435/320.1; 435/194; 435/195
[58] Field of Search ................................ 536/23.5, 24.31, 536/24.3; 435/69.1, 252.3, 320.1, 194, 195

[56] References Cited

PUBLICATIONS

Swan, A. et al., "Submicroscopic crystals in osteoarthritic synovial fluids" *Ann.Rheum.Dis.* (1994) 53:467–470.

Lohmander, L.S. et al., "Metalloproteinases, Tissue Inhibitor, and Proteoglycan Fragments in Knee Synovial Fluid in Human Osteoarthritis" *Arthritis Rheum.* (1993) 36:181–189.

Ryan, L.M. et al., "Adenosine Triphosphate Levels in Human Plasma" *J.Rheumatol.* (1996) 23:214–219.

Park, W. et al., "Inorganic Pyrophosphate Generation from Adenosine Triphosphate by Cell–Free Human Synovial Fluid" *J.Rheumatol.* (1996) 23:665–671.

Derfus, B.A. et al., "Articular Cartilage Vesicles Generate Calcium Pyrophosphate Dihydrate–Like Crystals In Vitro" *Arthritis Rheum.* (1992) 35:231–240.

Cardenal, A. et al., "Identification of a Nucleotide Pyrophosphohydrolase From Articular Tissues In Human Serum" *Arthritis Rheum.* (1996) 39:252–256.

Cardenal, A. et al., "Specificity of a Procine 127–KD Nucleotide Pyrophosphohydrolase for Articular Tissues" *Arthritis Rheum.* (1996) 39:245–251.

Hillier, L. et al., (GI 1515673), GenBank Sequence Database (Accession AA039396), National Center for Biotechnology Information, National Library of Medicine, Bethesda, Maryland, 20894.

Cottage, A. (GI 1070094) GenBank Sequence Database (Accession Z68011), National Center for Biotechnology Information, National Library of Medicine, Bethesda, Maryland, 20894. (GI 1070093).

Cottage, A. (GI 1070091), GenBank Sequence Database (Accession Z68011), National Center for Biotechnology Information, National Library of Medicine, Bethesda, Maryland, 20894. (GI 1070094).

Wilson, R. et al., "2.2 Mb of contiguous nucleotide sequence from chromosome III of *C. elegans*" *Nature* (1994) 368:32–381. (GI 1070093; GI 1070094).

*Primary Examiner*—Lila Feisee
*Assistant Examiner*—Geetha P. Bansal
*Attorney, Agent, or Firm*—Sheela Mohan-Peterson; Lucy J. Billings; Incyte Pharmaceuticals, Inc.

[57] ABSTRACT

The invention provides a human nucleotide pyrophosphohydrolase (NTPPH-1) and polynucleotides which identify and encode NTPPH-1. The invention also provides expression vectors, host cells, agonists, antibodies and antagonists. The invention also provides methods for treating disorders associated with expression of NTPPH-1.

13 Claims, 15 Drawing Sheets

```
5' NGC TGA GGA GTC CTG AAG ACA CGG TCA CTG GAT CTG AGA AAC TTC CCA GGG
                 9          18          27          36          45          54     108

GAC CGC ATT CCA GAG CTC GTC ACT CTG TGA AGC ACC CAC ATC TAC CTC TTG CCA
         63          72          81          90          99         117          153    162

CGT TCC CAC GGG CTT GGG GGA AAG ATG GTG GGG ACC AAG GCC TGG GTG TTC TCC
        171                                M   V   G   T   K   A   W   V   F   S
                                                                                    216

TTC CTG GTC CTG GAA GTC ACA TCT GTG TTG GGG TTG AGA CAG ATG CTC ACC CAG
     F   L   V   L   E   V   T   S   V   L   G   L   R   Q   M   L   T   Q
                                                                                    270

TCA GTA AGA AGA GTC CAG CCT GGG CCT GGT TAC GAG AGA CAG CCC AGC ATC TTT GCC ATC GAC TAC
     S   V   R   R   V   Q   P   G   P   G   Y   E   R   Q   P   S   I   F   A   I   D   Y
                                                                                    324

GCC GAC ACC CTG GAG AGC GAG TGG TGG ACA GAC GCC ATT CGC ACC TTC TAC TAT GGG
     A   D   T   L   E   S   E   W   W   T   D   A   I   R   T   F   Y   Y   G
                                                                                    378

CCA GGC AAG GGC GAC TAT CGG CTG CGG CTA GAG CTT AGA ACT GAC TGG ACA
     P   G   K   G   D   Y   R   L   R   L   E   L   A   R   T   D   W   T
                                                                                    432

GAC CGT GTA TGT GCC CGT CCC CGG CTA CGG CTT CAT GGT GTC CAT GGT GTT CAT GGT GTC CAT GAG GGT TTC TGG
     D   R   V   C   A   R   P   R   L   R   L   H   G   V   H   G   V   Q   V   H   G   V   H   E   G   F   W
                                                                                    486

CCT GCG GGC AGC ACT GGC CAG GTG CAT GGT GAG GGT TTC TGG
     P   A   G   S   T   G   Q   V   H   G   E   G   F   W
```

FIGURE 1A

```
495         504         513         522         531         540
TGC CTC AAC AGG GAG CAG CGG CCT GGC CAG AAC TGC TCT AAT TAC ACC GTA CGC
 C   L   N   R   E   Q   R   P   G   Q   N   C   S   N   Y   T   V   R 549         558         567         576         585         594
TTC CTC TGC CCA CCA TCC CTG CGC CGA GAC ACA GAG CGC ATC TGG AGC CCA
 F   L   C   P   P   S   L   R   R   D   T   E   R   I   W   S   P 603         612         621         630         639         648
TGG TCT CCC TGG AGC AAG TGC TCA GCT GCC TGT GGT CAG ACT GGG GTC CAG ACT
 W   S   P   W   S   K   C   S   A   A   C   G   Q   T   G   V   Q   T 657         666         675         684         693         702
CGC ACA CGC ATT TGC TTG GCA GAG ATG GTG TCG CTG TGC AGT GAG GCC AGC GAA
 R   T   R   I   C   L   A   E   M   V   S   L   C   S   E   A   S   E 711         720         729         738         747         756
GAG GGT CAG CAC TGC ATG GGC CAG GAC TGT ACA GCC TGT GAC CTG ACC TGC CCA
 E   G   Q   H   C   M   G   Q   D   C   T   A   C   D   L   T   C   P 765         774         783         792         801         810
ATG GGC CAG GTG AAT GCT GAC TGT GGA GCC CCA GCC TGC ATG GAC TTC ATG CTT
 M   G   Q   V   N   A   D   C   G   A   P   A   C   M   D   F   M   L 819         828         837         846         855         864
CAT GGG GCT GTC TCC CTT CCC AAG ACG CAG ACC TCA GCC GCT CTG ACC TGC TAC
 H   G   A   V   S   L   P   K   T   Q   T   S   A   A   L   T   C   Y 873         882         891         900         909         918
CTC ACC AAG ACC CCG AAG CTG ACC ACA GAC AGT GAT GGC GCT GCT ATC TTC ATG
 L   T   K   T   P   K   L   T   T   D   S   D   G   A   A   I   F   M 927         936         945         954         963         972
CGA ATC CCT GGC TGT CCT GAT GGC AAA AGC ATC CTG AAG ATC ACA AAG GTC
 R   I   P   G   C   P   D   G   K   S   I   L   K   I   T   K   V
```

FIGURE 1B

```
     981        990        999       1008       1017       1026
AAG TTT GCC  CCC ATT GTA  CTC ACA ATG  CCC AAG ACT  AGC CTG AAG  GCA GCC ACC
 K   F   A    P   I   V    L   T   M    P   K   T    S   L   K    A   A   T 1035       1044       1053       1062       1071       1080
ATC AAG GCA  GAG TTT GTG  AGG GCA GAG  ACT TAC CCA  GAG ATG GTG  ATG AAC CCT GAG
 I   K   A    E   F   V    R   A   E    T   Y   P    E   M   V    M   N   P   E 1089       1098       1107       1116       1125       1134
ACA AAA GCA  CGG AGA GCT  GGG CAG AGC  GTG TCT CTG  TGT TGT AAG  GCC ACA GGG
 T   K   A    R   R   A    G   Q   S    V   S   L    C   C   K    A   T   G 1143       1152       1161       1170       1179       1188
AAG CCC AGG  CCA GAC AAG  TAT TTT TGG  TAT CAT AAT  GAC ACA TTG  CTG GAT CCT
 K   P   R    P   D   K    Y   F   W    Y   H   N    D   T   L    L   D   P 1197       1206       1215       1224       1233       1242
TCC CTC TAC  AAG CAT GTC  ATA GCA GAG  AGC CTG GTG  CTG AAA AGG  CTG CAG CAC CAG
 S   L   Y    K   H   V    I   A   E    S   L   V    L   K   R    L   Q   H   Q 1251       1260       1269       1278       1287       1296
GCT GGG GAG  TAC TTT ATC  CGG CTG ATT  TGC AAG CAG  AGT GAT GCT  GGG CTG GTG AAG TCC AAG
 A   G   E    Y   F   I    R   L   I    C   K   Q    S   D   A    G   L   V   K   S   K 1305       1314       1323       1332       1341       1350
GTT GCC CAG  CTG ATT GTC  ATA GCA TCT  GAT GAG ACT  CCT TGC AAC  CCA GTT CCT
 V   A   Q    L   I   V    I   A   S    D   E   T    P   C   N    P   V   P 1359       1368       1377       1386       1395       1404
GAG AGC TAT  CTT ATC CGG  CTG CCC CAT  GAT TGC TTT  CAG AAT GCC  ACC AAC TCC
 E   S   Y    L   I   R    L   P   H    D   C   F    Q   N   A    T   N   S 1413       1422       1431       1440       1449       1458
TTC TAC TAT  GAC GTG GGA  CGC TGC CCT  GTT AAG ACT  TGT CCA GGG  CAG CAG GAT
 F   Y   Y    D   V   G    R   C   P    V   K   T    C   P   G    Q   Q   D
```

FIGURE 1C

```
                1467        1476        1485        1494        1503        1512
AAT GGG ATC AGG TGC CGT GAT GCT GTG CAG AAC TGC TGT GGC ATC TCC AAG ACA
 N   G   I   R   C   R   D   A   V   Q   N   C   C   G   I   S   K   T
                1521        1530        1539        1548        1557        1566
GAG GAA AGG GAG ATC CAG TGC AGT GGC TAC ACG CTA CCC ACC AAG GTG GCC AAG
 E   E   R   E   I   Q   C   S   G   Y   T   L   P   T   K   V   A   K
                1575        1584        1593        1602        1611        1620
GAG TGC AGC TGC CAG CGG TGT ACG CGG TGT ACG AGC ATC GTG CGG GGC CGT GTC
 E   C   S   C   Q   R   C   T   R   C   T   S   I   V   R   G   R   V
                1629        1638        1647        1656        1665        1674
AGT GCT GAC AAT GGG GAG CCC ATG CGC TTT GGC CAT GTG TAC ATG GGG AAC
 S   A   D   N   G   E   P   M   R   F   G   H   V   Y   M   G   N
                1683        1692        1701        1710        1719        1728
AGC CGT GTA AGC ATG ACT GGC TAC AAG GGC ACT TTC ACC CTC CAT GTC CCC CAG
 S   R   V   S   M   T   G   Y   K   G   T   F   T   L   H   V   P   Q
                1737        1746        1755        1764        1773        1782
GAC ACT GAG AGG CTG GTG CTC ACA TTT GTG GAC AGG CTG CAG AAG TTT GTC AAC
 D   T   E   R   L   V   L   T   F   V   D   R   L   Q   K   F   V   N
                1791        1800        1809        1818        1827        1836
ACC ACC AAA GTG CTA CCT TTC AAC AAG AAG GGG AGT GCC GTG TTC CAT GAA ATC
 T   T   K   V   L   P   F   N   K   K   G   S   A   V   F   H   E   I
                1845        1854        1863        1872        1881        1890
AAG ATG CTT TGT CGG AAA GAG CCC ATC ACT TTG GAA GCC ATG GAG ACC AAC ATT
 K   M   L   C   R   K   E   P   I   T   L   E   A   M   E   T   N   I
                1899        1908        1917        1926        1935        1944
ATC CCC CTG GGG GAA GTG GTT GGT GAA GAC CCC ATG GCT GAA CTG GAG ATT CCA
 I   P   L   G   E   V   V   G   E   D   P   M   A   E   L   E   I   P
```

FIGURE 1D

```
                  1953      1962      1971      1980      1989      1998
TCC AGG AGT TTC TAC AGG CAG AAT GGG GAG CCC TAC ATA GGA AAA GTG AAG GCC
 S   R   S   F   Y   R   Q   N   G   E   P   Y   I   G   K   V   K   A
                  2007      2016      2025      2034      2043      2052
AGT GTG ACC TTC CTG GAT CCC CGG AAT ATT TCC ACA GCC ACA GCT GCC CAG ACT
 S   V   T   F   L   D   P   R   N   I   S   T   A   T   A   A   Q   T
                  2061      2070      2079      2088      2097      2106
GAC CTG AAC TTC ATC AAT GAC GAA GGA GAC ACT TTC CCC CTT CGG ACG TAT GGC
 D   L   N   F   I   N   D   E   G   D   T   F   P   L   R   T   Y   G
                  2115      2124      2133      2142      2151      2160
ATG TTC TCT GTG GAC TTC AGA GAT GAG GTC ACC TCA GAG CCA CTT AAT GCT GGC
 M   F   S   V   D   F   R   D   E   V   T   S   E   P   L   N   A   G
                  2169      2178      2187      2196      2205      2214
AAA GTG AAG GTC CAC CTT GAC ACC CAG GTC AAG ATG CCA GAG CAC ATA TCC
 K   V   K   V   H   L   D   T   Q   V   K   M   P   E   H   I   S
                  2223      2232      2241      2250      2259      2268
ACA GTG AAA CTC TGG TCA CTC GAC AAT CCA GAC AGG AAC AAA AGA GAG ATG CCA GGG
 T   V   K   L   W   S   L   D   N   P   D   R   N   K   R   E   M   P   G
                  2277      2286      2295      2304      2313      2322
GAT TTC AAA TTT GAA AAT CAA AGG AGG AAC AAA AGA GAA GAC AGA ACC TTC CTG
 D   F   K   F   E   N   Q   R   R   N   K   R   E   D   R   T   F   L
                  2331      2340      2349      2358      2367      2376
GTG GGC AAC CTG GAG ATT CGT GAG AGG CTC TTT AAC CTG GAT GTT CCT GAA
 V   G   N   L   E   I   R   E   R   L   F   N   L   D   V   P   E
                  2385      2394      2403      2412      2421      2430
AGC AGG CGG TGC TTT GTT AAG GTG AGG AGG GCC TAC CGG AGT GAG AGG TTG CCT
 S   R   R   C   F   V   K   V   R   R   A   Y   R   S   E   R   L   P
```

```
2439        2448        2457        2466        2475        2484
AGT GAG ATC CAG CAG ATC TCC GTG ATT AAC CTG GAG CCT AGA ACT
 S   E   I   Q   Q   I   S   V   I   N   L   E   P   R   T 2493        2502        2511        2520        2529        2538
GGC TTC TTG TCC AAC CCT AGG GCC TGG GGC CGC TTT GAC AGT GTC ATC ACA GGC
 G   F   L   S   N   P   R   A   W   G   R   F   D   S   V   I   T   G 2547        2556        2565        2574        2583        2592
CCC AAC GGG GCC TGT GTG CCT GCC TTC TGT GAT GAC CAG TCC CCT GAT GCC TAC
 P   N   G   A   C   V   P   A   F   C   D   D   Q   S   P   D   A   Y 2601        2610        2619        2628        2637        2646
TCT GCC TAT GTC TTG GCA AGC CTG GCT GGG GAG GAA CTG CAA GCA GTG GAG TCT
 S   A   Y   V   L   A   S   L   A   G   E   E   L   Q   A   V   E   S 2655        2664        2673        2682        2691        2700
TCT CCT AAA TTC AAC CCA AAT GCA ATT GGC GTC CCT CAG CCC TAT CTC AAC AAG
 S   P   K   F   N   P   N   A   I   G   V   P   Q   P   Y   L   N   K 2709        2718        2727        2736        2745        2754
CTC AAC TAC CGT CGG ACG GAC CAT GAG GAT CCA CGG GTT AAA AAG ACA GCT TTC
 L   N   Y   R   R   T   D   H   E   D   P   R   V   K   K   T   A   F 2763        2772        2781        2790        2799        2808
CAG ATT AGC ATG GCC AAG CCA AGG CCC AAC TCA GCT GAG GAG AGC AAT GGG CCC
 Q   I   S   M   A   K   P   R   P   N   S   A   E   E   S   N   G   P 2817        2826        2835        2844        2853        2862
ATC TAT GCC TTT GAG AAC CTC CGG GCA TGT GAA GAG GCA CCA CCC AGT GCA GCC
 I   Y   A   F   E   N   L   R   A   C   E   E   A   P   P   S   A   A 2871        2880        2889        2898        2907        2916
CAC TTC CGG TTC TAC TAC CAG ATT GAG GGG GAT CGA TAT GAC TAC AAC ACA GTC CCC
 H   F   R   F   Y   Y   Q   I   E   G   D   R   Y   D   Y   N   T   V   P
```

```
                2925           2934           2943           2952           2961           2970
TTC AAC GAA GAT GAC CCT ATG AGC TGG ACT GAA GAC TAT CTG GCA TGG TGG CCA
 F   N   E   D   D   P   M   S   W   T   E   D   Y   L   A   W   W   P
                2979           2988           2997           3006           3015           3024
AAG CCG ATG GAA TTC AGG GCC TGC TAT ATC AAG GTG AAG ATT GTG GGG CCA CTG
 K   P   M   E   F   R   A   C   Y   I   K   V   K   I   V   G   P   L
                3033           3042           3051           3060           3069           3078
GAA GTG AAT GTG CGA TCC CGC AAC ATG GGG GGC ACT CAT CGG CGG ACA GTG GGG
 E   V   N   V   R   S   R   N   M   G   G   T   H   R   R   T   V   G
                3087           3096           3105           3114           3123           3132
AAG CTG TAT GGA ATC CGA GAT GTG AGG AGC ACT CGG GAC AGG GAC CAG CCC AAT
 K   L   Y   G   I   R   D   V   R   S   T   R   D   R   D   Q   P   N
                3141           3150           3159           3168           3177           3186
GTC TCA GCT GCC TGT CTG GAG TTC AAG TGC AGT GGG ATG CTC TAT GAT CAG GAC
 V   S   A   A   C   L   E   F   K   C   S   G   M   L   Y   D   Q   D
                3195           3204           3213           3222           3231           3240
CGT GTG GAC CGC CTG ACC CTG AAG GTG ATC CCC CAG GGC AGC TGC CGT CGA GCC
 R   V   D   R   L   T   L   K   V   I   P   Q   G   S   C   R   R   A
                3249           3258           3267           3276           3285           3294
AGT GTG AAC CCC ATG CTG CAT GAG TAC CTG GTC AAC CAC TTG CCA CTT GCA GTC
 S   V   N   P   M   L   H   E   Y   L   V   N   H   L   P   L   A   V
                3303           3312           3321           3330           3339           3348
AAC GAC ACC AGT GAG TAC ACC ATG CTG GCA CCC TTG GAC CCA CTG GGC CAC CAC
 N   D   T   S   E   Y   T   M   L   A   P   L   D   P   L   G   H   H
                3357           3366           3375           3384           3393           3402
AAC TAT GGC ATC TAC ACT GTC ACT GAC CAG GAC CCT CGC ACG GCC AAG GAG ATC
 N   Y   G   I   Y   T   V   T   D   Q   D   P   R   T   A   K   E   I
```

FIGURE 1G

```
            3411            3420            3429            3438            3447            3456
GCG CTC GGC CGG TGC TTT GAT GGC ACA TCC GAT GGC TCC TCC AGA ATC ATG AAG
 A   L   G   R   C   F   D   G   T   S   D   G   S   S   R   I   M   K
            3465            3474            3483            3492            3501            3510
AGC AAT GTG GGA GTA GCC CTC ACC TTC AAC TGT GTA GAG AGG CAA GTA GGC CGC
 S   N   V   G   V   A   L   T   F   N   C   V   E   R   Q   V   G   R
            3519            3528            3537            3546            3555            3564
CAG AGT GCC TTC CAG TAC CTC CAA AGC ACC CCA GCC CAG TCC CCT GCA GGA
 Q   S   A   F   Q   Y   L   Q   S   T   P   A   Q   S   P   A   G
            3573            3582            3591            3600            3609            3618
ACT GTC CAA GGA AGA GTG CCC TCG AGG AGG CAG CAG CGA GCG AGC AGG GGT GGC
 T   V   Q   G   R   V   P   S   R   R   Q   Q   R   A   S   R   G   G
            3627            3636            3645            3654            3663            3672
CAG CGC CAG AGT GGA GTG GTG GCC TCT CTG AGA TTT CCT AGA GTT GCT CAA CAG
 Q   R   Q   S   G   V   V   A   S   L   R   F   P   R   V   A   Q   Q
            3681            3690            3699            3708            3717            3726
CCC CTG ATC AAC TAA GTT TTG TGG TAC TTC ACC TTC TGC CCT CAT TTC ATG
 P   L   I   N   *
            3735            3744            3753            3762            3771            3780
TGA CAG CCA TTG TGA GAC TGA TGC ACA AAC TGT CAC TTG GTT AAT TTA AGC ACT
            3789            3798            3807            3816            3825            3834
TCT GTT TTC GTG AAT TTG CTT GTT TGT TTC TTC ATG CCT TTA CTT ACT TTG TCC
            3843            3852            3861            3870            3879            3888
CAT GCT ACT GAT TGG CAC GTG GCC CCC ACA ATG GCA CAA TAA AGC CCC TTT GTG
            3897            3906            3915            3924            3933            3942
AAA CTG TTC TTT AAA TGA AAC ACA AGA AAT TGG CCA CTG AAA CTC TGC AGC
```

FIGURE 1H

```
       3951      3960      3969      3978      3987      3996
TTC AAC TGT ACT TCA TTT AAT GCC ATT AAT ATA CTT CCT CTT TTT
       4005      4014      4023      4032      4041      4050
GCA TGG TTT TGC CCA CCT CTG CAA TAG TGA TAA TCT GAT GCT GAA GAT CAA ATA
       4059      4068      4077      4086      4095      4104
ACC AAT ATA AAG CAT ATT TCT TGG CCT TGC TCC ACA GGA CAT AGG CAA GCC TTG
       4113      4122      4131      4140      4149      4158
ATC ATA GTT CAT ACA TAT AAA TGG TGG TGA AAT AAA GAA ATA AAA CAC AAT ACT
       4167      4176      4185      4194      4203      4212
TTT ACT TGA AAT GTA AAT AAC TTA TTT ATT TCT TTG CTA AAT TTG GAA TTC TAG
       4221      4230      4239      4248      4257      4266
TGC ACA TTC AAA GTT AAG CTA TTA AAT ATA GGG TGA TCA TAG TTC CTC TAC CAA
       4275      4284      4293      4302      4311      4320
GTC TGG AAA GAA CAT CTC CTG GTA TCC ACA ATT ACA CCA GGT TGC TAA CTG TAT
       4329      4338      4347      4356      4365      4374
TTG TAC ATT TCC CTT TGC ATT CGC TTT TGT TCT TGC TAG AAA CCC AGT GTA GCC
       4383      4392      4401      4410      4419      4428
CAG GGC AGA TGT CAA TAA ATG CAT ACT CTG TAT TTC GAA AAA AAA AAA AAA AAA
AAA 3'
```

FIGURE 1I

```
>GI1515673 PubEST (2/1/97)

HNTPPH:    1   MVGTKAWVFSFLVLEVTSVLG  21
               MVGTKAWVFSFLVLEVTSVLG
GI 1515673:  86 MVGTKAWVFSFLVLEVTSVLG 148

>GI1070094  T21B6.3 [Caenorhabditis elegans]    Length = 788

HNTPPH:  151 IWSPWSPWSKCSAACG 166
             +WSPW  WS CSA+CG
T21B6.3: 605 LWSPWQEWSTCSASCG 620

HNTPPH:  153 SPWSPWSKCSAACGQTGVQTRTRICLAEMVSLCSEASEEGQHCMGQDCTACDLTCPMGQV 212
             S WSPW + S      G    + R  +  + C   +EE Q C G  C      C
T21B6.3: 604 SLWSPWQEWSTCSASCGSGMKRRQRVCQFGTDCQGPNEESQFCYGPPCAEWTEWCEWSGC 663

HNTPPH:  213 NADC 216
             ++ C
T21B6.3: 664 SSKC 667

HNTPPH:  152 WSPWSPWSKCSAACG 166
             WS W  WS CSA+CG
T21B6.3: 505 WSEWCEWSTCSASCG 51
```

Figure 2A

```
HNTPPH:  152 WSPWSPWSKCSAACGQ 167
             WS W  W +CS  CGQ
T21B6.3: 554 WSQWEDWGQCSVTCGQ 569

HNTPPH:  151 IWSPWSPWSKCSAACG 166
             +W  WS WS CS  CG
Sbjct:   457 VWHDWSDWSTCSCTCG 472

HNTPPH:  167 QTGVQTRTRICLAEMVSLCSEASEEGQHCMG 197
             + GVQ+R+R C+ E    C   +EE Q C G
T21B6.3: 748 EVGVQSRSRQCVGESGCHCIGLAEESQQCRG 778

HNTPPH:  152 WSPWSPWSKCSAACG 166
             W+ W  WS CS+ CG
T21B6.3: 654 WTEWCEWSGCSSKCG 668

HNTPPH:  152 WSPWSPWSKCSAACG 166
             WS W  WS C   CG
T21B6.3: 707 WSEWCHWSMCDKECG 721

HNTPPH:   48 DTLESPGEWTTW  59
             +  +E   G+WT W
Sbjct:   156 EAVEGVGDWTDW 167
```

Figure 2B

```
HNTPPH:  185  CSEASEEGQHCMGQDCTACDLTCPMGQVNADC  216
              C  SE   C GQ C    C   + +C
T21B6.3: 689  CQGPSIETTLCEGQSCCNWSEWCHWSMCDKEC  720

HNTPPH:  923  DYNTVPFNEDDPMSWTE  939
              DY  T P N    +W+E
T21B6.3: 491  DYETEPCNLGPCQTWSE  507

HNTPPH:   55  EWTTWFNIDYPGGKGDYER   73
              EW  W     G G  ER
T21B6.3: 507  EWCEWSTCSASCGSGQRER  525

HNTPPH:   97  TDWTPAGSTGQVVHGSPRE  115
              TDW+    S G V    E
T21B6.3: 165  TDWSHCSSNGHEVRSQACE  183

HNTPPH:  169  GVQTRTRICL  178
              G +TRTR CL
T21B6.3: 670  GQRTRTRGCL  679
```

Figure 2C

| | | | |
|---|---|---|---|
| Urinary System | 7 | Skin | 3 |
| 1600522 BLADNOT03 | | 2027529 KERANOT02 | |
| 1672908 BLADNOT05 | | 2619522 KERANOT02 | |
| 1720127 BLADNOT06 | | 1867994 SKINBIT01 | |
| 1315862 BLADTUT02 | | Immunological Tissues | 6 |
| 1315885 BLADTUT02 | | 511759 MPHGNOT03 | |
| 1519008 BLADTUT04 | | 512331 MPHGNOT03 | |
| 1658813 URETTUT01 | | 2754113 THP1AZS08 | |
| Nervous System | 8 | 2757313 THP1AZS08 | |
| 2151939 BRAINOT09 | | 2752911 THP1AZS08 | |
| 495383 HNT2NOT01 | | 3003863 TLYMNOT06 | |
| 2417170 HNT3AZT01 | | Female Tissues | |
| 2308490 NGANNOT01 | | 915156 BRSTNOT04 | 8 |
| 1365096 SCORNON02 | | 1967480 BRSTNOT04 | |
| 673553 CRBLNOT01 | | 3090087 BRSTNOT19 | |
| 675530 CRBLNOT01 | | 1212343 BRSTTUT01 | |
| 91399 HYPONOB01 | | 1216325 BRSTTUT01 | |
| Gastrointestinal Tissues | 16 | 2116311 BRSTTUT02 | |
| 1282063 COLNNOT16 | | 1998288 BRSTTUT03 | |
| 1933177 COLNNOT16 | | 2740094 BRSTTUT14 | |
| 1799116 COLNNOT27 | | 2325703 OVARNOT02 | 8 |
| 3236629 COLNUCT03 | | 2321280 OVARNOT02 | |
| 1909590 CONNTUT01 | | 2321023 OVARNOT02 | |
| 3228791 COTRNOT01 | | 544604 OVARNOT02 | |
| 3230462 COTRNOT01 | | 798386 OVARNOT03 | |
| 1579104 DUODNOT01 | | 3252733 OVARTUN01 | |
| 1703165 DUODNOT02 | | 2778952 OVARTUT03 | |
| 2530317 GBLANOT02 | | 589919 UTRSNOT01 | |
| 2069438 ISLTNOT01 | | Male Tissues | |
| 2050505 LIVRFET02 | | 3204894 PENCNOT03 | 9 |
| 1516083 PANCTUT01 | | 3276926 PROSBPT06 | |
| 1513351 PANCTUT01 | | 3354511 PROSNOT28 | |
| 1426966 SINTBST01 | | 833463 PROSTUT04 | |
| 1748149 STOMTUT02 | | 2625935 PROSTUT12 | |
| Cardiovascular Tissues | 12 | 2007636 TESTNOT03 | |
| 875815 LUNGAST01 | | 2005772 TESTNOT03 | |
| 1510677 LUNGNOT14 | | 3218636 TESTNOT07 | |
| 2686820 LUNGNOT23 | | 1275822 TESTTUT02 | |
| 2456587 ENDANOT01 | | Synovial Tissues | 6 |
| 2176245 ENDCNOT03 | | 722385 SYNOOAT01 | |
| 2970982 HEAONOT02 | | 726136 SYNOOAT01 | |
| 3330575 HEAONOT04 | | 721889 SYNOOAT01 | |
| 2474895 SMCANOT01 | | 718608 SYNOOAT01 | |
| 2478137 SMCANOT01 | | 1264296 SYNORAT05 | |
| 1562795 SPLNNOT04 | | 1265186 SYNORAT05 | |
| 3336346 SPLNNOT10 | | 2344658 TESTTUT02 | |
| 3337876 SPLNNOT10 | | Glandular Tissues | 4 |
| Muscle | 2 | 2495178 ADRETUT05 | |
| 984059 TONGTUT01 | | 2494632 ADRETUT05 | |
| 984063 TONGTUT01 | | 2875481 THYRNOT10 | |
| | | 2872569 THYRNOT10 | |

FIGURE 5

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1184 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: ???
        ( B ) CLONE: 422069

( x i ) SEQUENCE DESCRIPTION: SEQ ID NO:1:

```
Met Val Gly Thr Lys Ala Trp Val Phe Ser Phe Leu Val Leu Glu Val
  1               5               10              15
Thr Ser Val Leu Gly Arg Gln Thr Met Leu Thr Gln Ser Val Arg Arg
              20              25              30
Val Gln Pro Gly Lys Lys Asn Pro Ser Ile Phe Ala Lys Pro Ala Asp
          35              40              45
Thr Leu Glu Ser Pro Gly Glu Trp Thr Thr Trp Phe Asn Ile Asp Tyr
      50              55              60
Pro Gly Gly Lys Gly Asp Tyr Glu Arg Leu Asp Ala Ile Arg Phe Tyr
 65              70              75              80
Tyr Gly Asp Arg Val Cys Ala Arg Pro Leu Arg Leu Glu Ala Arg Thr
              85              90              95
Thr Asp Trp Thr Pro Ala Gly Ser Thr Gly Gln Val Val His Gly Ser
            100             105             110
Pro Arg Glu Gly Phe Trp Cys Leu Asn Arg Glu Gln Arg Pro Gly Gln
          115             120             125
Asn Cys Ser Asn Tyr Thr Val Arg Phe Leu Cys Pro Pro Gly Ser Leu
        130             135             140
Arg Arg Asp Thr Glu Arg Ile Trp Ser Pro Ser Pro Trp Ser Lys
145             150             155             160
Cys Ser Ala Ala Cys Gly Gln Thr Gly Val Gln Thr Arg Thr Arg Ile
              165             170             175
Cys Leu Ala Glu Met Val Ser Leu Cys Ser Glu Ala Ser Glu Glu Gly
            180             185             190
Gln His Cys Met Gly Gln Asp Cys Thr Ala Cys Asp Leu Thr Cys Pro
        195             200             205
Met Gly Gln Val Asn Ala Asp Cys Asp Ala Cys Met Cys Gln Asp Phe
210             215             220
Met Leu His Gly Ala Val Ser Leu Pro Gly Gly Ala Pro Ala Ser Gly
225             230             235             240
Ala Ala Ile Tyr Leu Leu Thr Lys Thr Pro Lys Leu Leu Thr Gln Thr
              245             250             255
Asp Ser Asp Gly Arg Phe Arg Ile Pro Gly Leu Cys Pro Asp Gly Lys
            260             265             270
Ser Ile Leu Lys Ile Thr Lys Val Lys Phe Ala Pro Ile Val Leu Thr
        275             280             285
Met Pro Lys Thr Ser Leu Lys Ala Ala Thr Ile Lys Ala Glu Phe Val
290             295             300
Arg Ala Glu Thr Pro Tyr Met Val Met Asn Pro Glu Thr Lys Ala Arg
305             310             315             320
Arg Ala Gly Gln Ser Val Ser Leu Cys Cys Lys Ala Thr Gly Lys Pro
              325             330             335
Arg Pro Asp Lys Tyr Phe Trp Tyr His Asn Asp Thr Leu Leu Asp Pro
            340             345             350
Ser Leu Tyr Lys His Glu Ser Lys Leu Val Leu Arg Lys Leu Gln Gln
        355             360             365
His Gln Ala Gly Glu Tyr Phe Cys Lys Ala Gln Ser Asp Ala Gly Ala
        370             375             380
Val Lys Ser Lys Val Ala Gln Leu Ile Val Ile Ala Ser Asp Glu Thr
385             390             395             400
Pro Cys Asn Pro Val Pro Glu Ser Tyr Leu Ile Arg Leu Pro His Asp
            405             410             415
Cys Phe Gln Asn Ala Thr Asn Ser Phe Tyr Tyr Asp Val Gly Arg Cys
            420             425             430
```

```
Pro  Val  Lys  Thr  Cys  Ala  Gly  Gln  Gln  Asp  Asn  Gly  Ile  Arg  Cys  Arg
          435                 440                 445

Asp  Ala  Val  Gln  Asn  Cys  Cys  Gly  Ile  Ser  Lys  Thr  Glu  Glu  Arg  Glu
          450                 455                 460

Ile  Gln  Cys  Ser  Gly  Tyr  Thr  Leu  Pro  Thr  Lys  Val  Ala  Lys  Glu  Cys
465                      470                 475                           480

Ser  Cys  Gln  Arg  Cys  Thr  Glu  Thr  Arg  Ser  Ile  Val  Arg  Gly  Arg  Val
               485                      490                           495

Ser  Ala  Ala  Asp  Asn  Gly  Glu  Pro  Met  Arg  Phe  Gly  His  Val  Tyr  Met
               500                 505                      510

Gly  Asn  Ser  Arg  Val  Ser  Met  Thr  Gly  Tyr  Lys  Gly  Thr  Phe  Thr  Leu
               515                 520                      525

His  Val  Pro  Gln  Asp  Thr  Glu  Arg  Leu  Val  Leu  Thr  Phe  Val  Asp  Arg
          530                 535                      540

Leu  Gln  Lys  Phe  Val  Asn  Thr  Thr  Lys  Val  Leu  Pro  Phe  Asn  Lys  Lys
545                      550                      555                      560

Gly  Ser  Ala  Val  Phe  His  Glu  Ile  Lys  Met  Leu  Cys  Arg  Lys  Glu  Pro
                    565                 570                      575

Ile  Thr  Leu  Glu  Ala  Met  Glu  Thr  Asn  Ile  Ile  Pro  Leu  Gly  Glu  Val
               580                 585                      590

Val  Gly  Glu  Asp  Pro  Met  Ala  Glu  Leu  Glu  Ile  Pro  Ser  Arg  Ser  Phe
          595                 600                      605

Tyr  Arg  Gln  Asn  Gly  Glu  Pro  Tyr  Ile  Gly  Lys  Val  Lys  Ala  Ser  Val
     610                 615                 620

Thr  Phe  Leu  Asp  Pro  Arg  Asn  Ile  Ser  Thr  Ala  Thr  Ala  Ala  Gln  Thr
625                      630                      635                      640

Asp  Leu  Asn  Phe  Ile  Asn  Asp  Glu  Gly  Asp  Thr  Phe  Pro  Leu  Arg  Thr
                    645                 650                      655

Tyr  Gly  Met  Phe  Ser  Val  Asp  Phe  Arg  Asp  Glu  Val  Thr  Ser  Glu  Pro
               660                 665                      670

Leu  Asn  Ala  Gly  Lys  Val  Lys  Val  His  Leu  Asp  Ser  Thr  Gln  Val  Lys
               675                 680                      685

Met  Pro  Glu  His  Ile  Ser  Thr  Val  Lys  Leu  Trp  Ser  Leu  Asn  Pro  Asp
     690                      695                 700

Thr  Gly  Leu  Trp  Glu  Glu  Gly  Asp  Phe  Lys  Phe  Glu  Asn  Gln  Arg
705                 710                 715                      720

Arg  Asn  Lys  Arg  Glu  Asp  Arg  Thr  Phe  Leu  Val  Gly  Asn  Leu  Glu  Ile
               725                      730                      735

Arg  Glu  Arg  Arg  Leu  Phe  Asn  Leu  Asp  Val  Pro  Glu  Ser  Arg  Arg  Cys
               740                      745                 750

Phe  Val  Lys  Val  Arg  Ala  Tyr  Arg  Ser  Glu  Arg  Phe  Leu  Pro  Ser  Glu
          755                 760                 765

Gln  Ile  Gln  Gly  Val  Val  Ile  Ser  Val  Ile  Asn  Leu  Glu  Pro  Arg  Thr
     770                 775                 780

Gly  Phe  Leu  Ser  Asn  Pro  Arg  Ala  Trp  Gly  Arg  Phe  Asp  Ser  Val  Ile
785                      790                 795                           800

Thr  Gly  Pro  Asn  Gly  Ala  Cys  Val  Pro  Ala  Phe  Cys  Asp  Asp  Gln  Ser
               805                      810                           815

Pro  Asp  Ala  Tyr  Ser  Ala  Tyr  Val  Leu  Ala  Ser  Leu  Ala  Gly  Glu  Glu
               820                 825                      830

Leu  Gln  Ala  Val  Glu  Ser  Ser  Pro  Lys  Phe  Asn  Pro  Asn  Ala  Ile  Gly
          835                 840                      845
```

Val Pro Gln Pro Tyr Leu Asn Lys Leu Asn Tyr Arg Arg Thr Asp His
850                     855                     860

Glu Asp Pro Arg Val Lys Thr Ala Phe Gln Ile Ser Met Ala Lys
865                     870                     875                     880

Pro Arg Pro Asn Ser Ala Glu Glu Ser Asn Gly Pro Ile Tyr Ala Phe
                885                     890                     895

Glu Asn Leu Arg Ala Cys Glu Glu Ala Pro Pro Ser Ala Ala His Phe
                900                     905                     910

Arg Phe Tyr Gln Ile Glu Gly Asp Arg Tyr Asp Tyr Asn Thr Val Pro
            915                     920                     925

Phe Asn Glu Asp Asp Pro Met Ser Trp Thr Glu Asp Tyr Leu Ala Trp
            930                     935                     940

Trp Pro Lys Pro Met Glu Phe Arg Ala Cys Tyr Ile Lys Val Lys Ile
945                     950                     955                     960

Val Gly Pro Leu Glu Val Asn Val Arg Ser Arg Asn Met Gly Gly Thr
                965                     970                     975

His Arg Arg Thr Val Gly Lys Leu Tyr Gly Ile Arg Asp Val Arg Ser
            980                     985                     990

Thr Arg Asp Arg Asp Gln Pro Asn Val Ser Ala Ala Cys Leu Glu Phe
            995                     1000                    1005

Lys Cys Ser Gly Met Leu Tyr Asp Gln Asp Arg Val Asp Arg Thr Leu
    1010                    1015                    1020

Val Lys Val Ile Pro Gln Gly Ser Cys Arg Arg Ala Ser Val Asn Pro
025                     1030                    1035                    1040

Met Leu His Glu Tyr Leu Val Asn His Leu Pro Leu Ala Val Asn Asn
                1045                    1050                    1055

Asp Thr Ser Glu Tyr Thr Met Leu Ala Pro Leu Asp Pro Leu Gly His
                1060                    1065                    1070

Asn Tyr Gly Ile Tyr Thr Val Thr Asp Gln Asp Pro Arg Thr Ala Lys
            1075                    1080                    1085

Glu Ile Ala Leu Gly Arg Cys Phe Asp Gly Thr Ser Asp Gly Ser Ser
    1090                    1095                    1100

Arg Ile Met Lys Ser Asn Val Gly Val Ala Leu Thr Phe Asn Cys Val
105                     1110                    1115                    1120

Glu Arg Gln Val Gly Arg Gln Ser Ala Phe Gln Tyr Leu Gln Ser Thr
                1125                    1130                    1135

Pro Ala Gln Ser Pro Ala Ala Gly Thr Val Gln Gly Arg Val Pro Ser
                1140                    1145                    1150

Arg Arg Gln Gln Arg Ala Ser Arg Gly Gly Gln Arg Gln Ser Gly Val
            1155                    1160                    1165

Val Ala Ser Leu Arg Phe Pro Arg Val Ala Gln Gln Pro Leu Ile Asn
    1170                    1175                    1180

( 2 ) INFORMATION FOR SEQ ID NO:2:

( i ) SEQUENCE CHARACTERISTICS:
        ( A ) LENGTH: 4430 base pairs
        ( B ) TYPE: nucleic acid
        ( C ) STRANDEDNESS: single
        ( D ) TOPOLOGY: linear ( v i i ) IMMEDIATE SOURCE:
        ( A ) LIBRARY: ???
        ( B ) CLONE: 422069

( x i ) SEQUENCE DESCRIPTION: SEQ ID NO:2:

GCTGAGGAGT CCTGCTCAAG ACACGGTCAC TGGATCTGAG AAACTTCCCA GGGGACCGCA 60

```
TTCCAGAGTC  AGTGACTCTG  TGAAGCACCC  ACATCTACCT  CTTGCCACGT  TCCCACGGGC   120

TTGGGGGAAA  GATGGTGGGG  ACCAAGGCCT  GGGTGTTCTC  CTTCCTGGTC  CTGGAAGTCA   180

CATCTGTGTT  GGGGAGACAG  ACGATGCTCA  CCCAGTCAGT  AAGAAGAGTC  CAGCCTGGGA   240

AGAAGAACCC  CAGCATCTTT  GCCAAGCCTG  CCGACACCCT  GGAGAGCCCT  GGTGAGTGGA   300

CAACATGGTT  CAACATCGAC  TACCCAGGCG  GGAAGGGCGA  CTATGAGCGG  CTGGACGCCA   360

TTCGCTTCTA  CTATGGGGAC  CGTGTATGTG  CCCGTCCCCT  GCGGCTAGAG  GCTCGGACCA   420

CTGACTGGAC  ACCTGCGGGC  AGCACTGGCC  AGGTGGTCCA  TGGTAGTCCC  CGTGAGGGTT   480

TCTGGTGCCT  CAACAGGGAG  CAGCGGCCTG  GCCAGAACTG  CTCTAATTAC  ACCGTACGCT   540

TCCTCTGCCC  ACCAGGATCC  CTGCGCCGAG  ACACAGAGCG  CATCTGGAGC  CCATGGTCTC   600

CCTGGAGCAA  GTGCTCAGCT  GCCTGTGGTC  AGACTGGGGT  CCAGACTCGC  ACACGCATTT   660

GCTTGGCAGA  GATGGTGTCG  CTGTGCAGTG  AGGCCAGCGA  AGAGGGTCAG  CACTGCATGG   720

GCCAGGACTG  TACAGCCTGT  GACCTGACCT  GCCCAATGGG  CCAGGTGAAT  GCTGACTGTG   780

ATGCCTGCAT  GTGCCAGGAC  TTCATGCTTC  ATGGGGCTGT  CTCCCTTCCC  GGAGGTGCCC   840

CAGCCTCAGG  GGCTGCTATC  TACCTCCTGA  CCAAGACGCC  GAAGCTGCTG  ACCCAGACAG   900

ACAGTGATGG  GAGATTCCGA  ATCCCTGGCT  TGTGCCCTGA  TGGCAAAAGC  ATCCTGAAGA   960

TCACAAAGGT  CAAGTTTGCC  CCCATTGTAC  TCACAATGCC  CAAGACTAGC  CTGAAGGCAG  1020

CCACCATCAA  GGCAGAGTTT  GTGAGGGCAG  AGACTCCATA  CATGGTGATG  AACCCTGAGA  1080

CAAAAGCACG  GAGAGCTGGG  CAGAGCGTGT  CTCTGTGCTG  TAAGGCCACA  GGGAAGCCCA  1140

GGCCAGACAA  GTATTTTGG   TATCATAATG  ACACATTGCT  GGATCCTTCC  CTCTACAAGC  1200

ATGAGAGCAA  GCTGGTGCTG  AGGAAACTGC  AGCAGCACCA  GGCTGGGGAG  TACTTTTGCA  1260

AGGCCCAGAG  TGATGCTGGG  GCTGTGAAGT  CCAAGGTTGC  CCAGCTGATT  GTCATAGCAT  1320

CTGATGAGAC  TCCTTGCAAC  CCAGTTCCTG  AGAGCTATCT  TATCCGGCTG  CCCCATGATT  1380

GCTTTCAGAA  TGCCACCAAC  TCCTTCTACT  ATGACGTGGG  ACGCTGCCCT  GTTAAGACTT  1440

GTGCAGGGCA  GCAGGATAAT  GGGATCAGGT  GCCGTGATGC  TGTGCAGAAC  TGCTGTGGCA  1500

TCTCCAAGAC  AGAGGAAAGG  GAGATCCAGT  GCAGTGGCTA  CACGCTACCC  ACCAAGGTGG  1560

CCAAGGAGTG  CAGCTGCCAG  CGGTGTACGG  AAACTCGGAG  CATCGTGCGG  GGCCGTGTCA  1620

GTGCTGCTGA  CAATGGGGAG  CCCATGCGCT  TTGGCCATGT  GTACATGGGG  AACAGCCGTG  1680

TAAGCATGAC  TGGCTACAAG  GGCACTTTCA  CCCTCCATGT  CCCCCAGGAC  ACTGAGAGGC  1740

TGGTGCTCAC  ATTTGTGGAC  AGGCTGCAGA  AGTTTGTCAA  CACCACCAAA  GTGCTACCTT  1800

TCAACAAGAA  GGGGAGTGCC  GTGTTCCATG  AAATCAAGAT  GCTTTGTCGG  AAAGAGCCCA  1860

TCACTTTGGA  AGCCATGGAG  ACCAACATTA  TCCCCCTGGG  GGAAGTGGTT  GGTGAAGACC  1920

CCATGGCTGA  ACTGGAGATT  CCATCCAGGA  GTTTCTACAG  GCAGAATGGG  GAGCCCTACA  1980

TAGGAAAAGT  GAAGGCCAGT  GTGACCTTCC  TGGATCCCCG  GAATATTTCC  ACAGCCACAG  2040

CTGCCCAGAC  TGACCTGAAC  TTCATCAATG  ACGAAGGAGA  CACTTTCCCC  CTTCGGACGT  2100

ATGGCATGTT  CTCTGTGGAC  TTCAGAGATG  AGGTCACCTC  AGAGCCACTT  AATGCTGGCA  2160

AAGTGAAGGT  CCACCTTGAC  TCGACCCAGG  TCAAGATGCC  AGAGCACATA  TCCACAGTGA  2220

AACTCTGGTC  ACTCAATCCA  GACACAGGGC  TGTGGGAGGA  GGAAGGTGAT  TTCAAATTTG  2280

AAAATCAAAG  GAGGAACAAA  AGAGAAGACA  GAACCTTCCT  GGTGGGCAAC  CTGGAGATTC  2340

GTGAGAGGAG  GCTCTTTAAC  CTGGATGTTC  CTGAAAGCAG  GCGGTGCTTT  GTTAAGGTGA  2400

GGGCCTACCG  GAGTGAGAGG  TTCTTGCCTA  GTGAGCAGAT  CCAGGGGGTT  GTGATCTCCG  2460
```

-continued

| | | | | | | |
|---|---|---|---|---|---|---|
| TGATTAACCT | GGAGCCTAGA | ACTGGCTTCT | TGTCCAACCC | TAGGGCCTGG | GGCCGCTTTG | 2520 |
| ACAGTGTCAT | CACAGGCCCC | AACGGGGCCT | GTGTGCCTGC | CTTCTGTGAT | GACCAGTCCC | 2580 |
| CTGATGCCTA | CTCTGCCTAT | GTCTTGGCAA | GCCTGGCTGG | GGAGGAACTG | CAAGCAGTGG | 2640 |
| AGTCTTCTCC | TAAATTCAAC | CCAAATGCAA | TTGGCGTCCC | TCAGCCCTAT | CTCAACAAGC | 2700 |
| TCAACTACCG | TCGGACGGAC | CATGAGGATC | CACGGGTTAA | AAAGACAGCT | TTCCAGATTA | 2760 |
| GCATGGCCAA | GCCAAGGCCC | AACTCAGCTG | AGGAGAGCAA | TGGGCCCATC | TATGCCTTTG | 2820 |
| AGAACCTCCG | GGCATGTGAA | GAGGCACCAC | CCAGTGCAGC | CCACTTCCGG | TTCTACCAGA | 2880 |
| TTGAGGGGGA | TCGATATGAC | TACAACACAG | TCCCCTTCAA | CGAAGATGAC | CCTATGAGCT | 2940 |
| GGACTGAAGA | CTATCTGGCA | TGGTGGCCAA | AGCCGATGGA | ATTCAGGGCC | TGCTATATCA | 3000 |
| AGGTGAAGAT | TGTGGGGCCA | CTGGAAGTGA | ATGTGCGATC | CCGCAACATG | GGGGGCACTC | 3060 |
| ATCGGCGGAC | AGTGGGGAAG | CTGTATGGAA | TCCGAGATGT | GAGGAGCACT | CGGGACAGGG | 3120 |
| ACCAGCCCAA | TGTCTCAGCT | GCCTGTCTGG | AGTTCAAGTG | CAGTGGGATG | CTCTATGATC | 3180 |
| AGGACCGTGT | GGACCGCACC | CTGGTGAAGG | TCATCCCCCA | GGGCAGCTGC | CGTCGAGCCA | 3240 |
| GTGTGAACCC | CATGCTGCAT | GAGTACCTGG | TCAACCACTT | GCCACTTGCA | GTCAACAACG | 3300 |
| ACACCAGTGA | GTACACCATG | CTGGCACCCT | TGGACCCACT | GGGCCACAAC | TATGGCATCT | 3360 |
| ACACTGTCAC | TGACCAGGAC | CCTCGCACGG | CCAAGGAGAT | CGCGCTCGGC | CGGTGCTTTG | 3420 |
| ATGGCACATC | CGATGGCTCC | TCCAGAATCA | TGAAGAGCAA | TGTGGGAGTA | GCCCTCACCT | 3480 |
| TCAACTGTGT | AGAGAGGCAA | GTAGGCCGCC | AGAGTGCCTT | CCAGTACCTC | CAAAGCACCC | 3540 |
| CAGCCCAGTC | CCCTGCTGCA | GGCACTGTCC | AAGGAAGAGT | GCCCTCGAGG | AGGCAGCAGC | 3600 |
| GAGCGAGCAG | GGGTGGCCAG | CGCCAGAGTG | GAGTGGTGGC | CTCTCTGAGA | TTTCCTAGAG | 3660 |
| TTGCTCAACA | GCCCCTGATC | AACTAAGTTT | TGTGGTACTT | CACCTTCTTC | TGCCCTCATT | 3720 |
| TCATGTGACA | GCCATTGTGA | GACTGATGCA | CAAACTGTCA | CTTGGTTAAT | TAAGCACTT | 3780 |
| CTGTTTTCGT | GAATTTGCTT | GTTTGTTTCT | TCATGCCTTT | ACTTACTTTG | TCCCATGCTA | 3840 |
| CTGATTGGCA | CGTGGCCCCC | ACAATGGCAC | AATAAAGCCC | TTTGTGAAA | CTGTTCTTTA | 3900 |
| AATGAAACAC | AAGAAATTGG | CCACTGGTAA | AACTCTGCAG | CTTCAACTGT | ACTTCATTTA | 3960 |
| ATGCCATTAA | TGCAAATATA | CTTCCTCTTC | TTTTTGCATG | GTTTTGCCCA | CCTCTGCAAT | 4020 |
| AGTGATAATC | TGATGCTGAA | GATCAAATAA | CCAATATAAA | GCATATTTCT | TGGCCTTGCT | 4080 |
| CCACAGGACA | TAGGCAAGCC | TTGATCATAG | TTCATACATA | TAAATGGTGG | TGAAATAAAG | 4140 |
| AAATAAAACA | CAATACTTTT | ACTTGAAATG | TAAATAACTT | ATTTATTTCT | TTGCTAAATT | 4200 |
| TGGAATTCTA | GTGCACATTC | AAAGTTAAGC | TATTAAATAT | AGGGTGATCA | TAGTTCCTCT | 4260 |
| ACCAAGTCTG | GAAAGAACAT | CTCCTGGTAT | CCACAATTAC | ACCAGGTTGC | TAACTGTATT | 4320 |
| TGTACATTTC | CCTTTGCATT | CGCTTTTGTT | CTTGCTAGAA | ACCCAGTGTA | GCCCAGGGCA | 4380 |
| GATGTCAATA | AATGCATACT | CTGTATTTCG | AAAAAAAAAA | AAAAAAAAA | | 4430 |

( 2 ) INFORMATION FOR SEQ ID NO:3:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 1515673

( x i ) SEQUENCE DESCRIPTION: SEQ ID NO:3:

Met Val Gly Thr Lys Ala Trp Val Phe Ser Phe Leu Val Leu Glu Val
1               5                   10                  15

Thr Ser Val Leu Gly Ile Gly
                20

(2) INFORMATION FOR SEQ ID NO:4:

(i) SEQUENCE CHARACTERISTICS:
        (A) LENGTH: 788 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1070094

(xi) SEQUENCE DESCRIPTION: SEQ ID NO:4:

Met Gln Ala Thr Val Gly Leu Phe Ala Leu Ala Val Leu Phe Cys Leu
1               5                   10                  15

Ala Asp Ala Gly Arg Ile Ser Val Ser Arg Gly Lys Asn Val Thr Lys
                20                  25                  30

Ile Asp Asp Leu Cys Ala Arg Met His Asn Asn Thr Ala Leu Glu Gly
                35                  40                  45

Ser Ser Pro Leu Leu Met Met Gln Ala Thr Ala Tyr Glu Cys Gln Lys
    50                  55                  60

Lys Cys Val Asp Ile Phe Pro Glu Cys Ser Ala Val Val Tyr Tyr Tyr
65                  70                  75                  80

Leu His Asn Glu Thr Lys Lys His Phe Cys Tyr Leu Phe Ser Asp Asn
                85                  90                  95

Ser Val Gln Asp Lys Ile Asp Leu Val Gln Lys Pro Glu Asn Lys
                100                 105                 110

Lys Asp Ile Val Arg Met Leu Glu Leu Val Val Asp Cys His Gln Phe
                115                 120                 125

Asp Ala His Pro Pro Leu Glu Glu Asp Gly Leu Ala Ser Ser Thr Asp
    130                 135                 140

Lys Val Asp Arg Lys Lys Arg Gln Gln Gly Asp Glu Ala Val Glu Gly
145                 150                 155                 160

Val Gly Asp Trp Thr Asp Trp Ser His Cys Ser Ser Asn Gly His Glu
                165                 170                 175

Val Arg Ser Gln Ala Cys Glu Tyr Gly Arg Lys Ile Gln Arg Arg Gly
                180                 185                 190

Cys Pro Ala Arg Ser Ala Pro Gln Arg Val Pro Ala Pro Pro Ala Gln
                195                 200                 205

Gln Tyr Ala Pro Arg Ala Pro Glu Tyr Pro Ser Ala Gln Gln Gln Gln
    210                 215                 220

Gln Gln Arg Glu Gln Gln Gln Arg Glu Gln Gln His Arg Glu His Gln
225                 230                 235                 240

Ala Arg Leu Gln Gln His Gln Gln Gln Gln Gln Gln Gln Gln Gln Gln
                245                 250                 255

Gln Gln Gln Arg Pro Pro Gln Pro Gln Pro Gln Pro Gln Pro Gln Pro
                260                 265                 270

Pro Gln Arg Pro Pro Gln Gln Pro Gln Ser Phe Ser Gly Thr His Glu
            275                 280                 285

Leu His Leu Gln Arg Gln Arg Glu Gln Gln Gln Gln Gln Gln Gln Gln
    290                 295                 300

```
Gln  Gln  Gln  Gln  Gln  Gln  Arg  Gln  Gln  Asn  Pro  Gln  Gln  Gln  Pro  Gln
305                      310                      315                      320

Gln  Thr  Thr  Gln  Phe  Gly  Gln  Ser  Gln  Ile  Gln  Leu  Gln  Ser  Gly  Pro
               325                      330                      335

Val  Pro  Pro  Gln  His  Pro  Gln  Gln  Pro  Gln  Gln  Pro  Gln  Gln  Gln  Pro
               340                      345                      350

Glu  Leu  Glu  Arg  Ser  Pro  Leu  Asp  Gln  His  Ala  Gln  Leu  Tyr  Gln  Gln
          355                      360                      365

Arg  Met  Ser  Gln  Tyr  Arg  Glu  Asn  Phe  Asn  Gln  Arg  His  Pro  Ala  Arg
          370                      375                      380

Pro  Lys  Ala  Asp  Pro  Cys  Pro  Gly  Gly  Phe  Cys  Ala  Pro  Val  Pro  Gln
385                      390                      395                      400

Ala  Pro  Gln  Gln  Glu  Arg  Pro  Thr  Pro  Pro  Val  Leu  Ala  Pro  Val
                    405                      410                      415

Ile  Asn  Thr  Ala  Thr  Gln  Pro  Pro  Leu  Pro  Gln  Pro  Tyr  Pro  Thr  Arg
               420                      425                      430

Tyr  Arg  Pro  Ala  Pro  Pro  Pro  Pro  Ala  Cys  Asp  Gly  Gln  Gly  Cys
          435                      440                      445

Val  Asn  Pro  Pro  Val  Val  Ser  Gly  Val  Trp  His  Asp  Trp  Ser  Asp  Trp
     450                      455                      460

Ser  Thr  Cys  Ser  Cys  Thr  Cys  Gly  Asp  Gly  Ala  Lys  Ser  Arg  Arg  Arg
465                      470                      475                      480

Glu  Cys  Ser  Thr  Asn  Asn  Cys  Gln  Gly  Ala  Asp  Tyr  Glu  Thr  Glu  Pro
                    485                      490                      495

Cys  Asn  Leu  Gly  Pro  Cys  Gln  Thr  Trp  Ser  Glu  Trp  Cys  Glu  Trp  Ser
               500                      505                      510

Thr  Cys  Ser  Ala  Ser  Cys  Gly  Ser  Gly  Gln  Arg  Glu  Arg  Thr  Arg  Phe
               515                      520                      525

Cys  His  Leu  Gly  Thr  Asn  Arg  Cys  Glu  Gly  Lys  Asp  Tyr  Glu  Ser  Glu
     530                      535                      540

Gln  Cys  Ser  Ala  Gly  Pro  Cys  Pro  Glu  Trp  Ser  Gln  Trp  Glu  Asp  Trp
545                      550                      555                      560

Gly  Gln  Cys  Ser  Val  Thr  Cys  Gly  Gln  Gly  Val  Ala  Val  Arg  Gln  Arg
               565                      570                      575

Thr  Cys  Leu  Gly  Gly  Val  Phe  Gly  Asp  His  Leu  Cys  Gln  Gly  Pro  Lys
               580                      585                      590

Thr  Glu  Gln  Arg  Ala  Cys  Asp  Gly  Gly  Pro  Cys  Ser  Leu  Trp  Ser  Pro
          595                      600                      605

Trp  Gln  Glu  Trp  Ser  Thr  Cys  Ser  Ala  Ser  Cys  Gly  Ser  Gly  Met  Lys
     610                      615                      620

Arg  Arg  Gln  Arg  Val  Cys  Gln  Phe  Gly  Thr  Asp  Cys  Gln  Gly  Pro  Asn
625                      630                      635                      640

Glu  Glu  Ser  Gln  Phe  Cys  Tyr  Gly  Pro  Pro  Cys  Ala  Glu  Trp  Thr  Glu
               645                      650                      655

Trp  Cys  Glu  Trp  Ser  Gly  Cys  Ser  Ser  Lys  Cys  Gly  Pro  Gly  Gln  Arg
          660                      665                      670

Thr  Arg  Thr  Arg  Gly  Cys  Leu  Gly  Pro  Asn  Gly  Gln  Glu  Ala  Thr  Thr
          675                      680                      685

Cys  Gln  Gly  Pro  Ser  Ile  Glu  Thr  Thr  Leu  Cys  Glu  Gly  Gln  Ser  Cys
     690                      695                      700

Cys  Asn  Trp  Ser  Glu  Trp  Cys  His  Trp  Ser  Met  Cys  Asp  Lys  Glu  Cys
705                      710                      715                      720

Gly  Gly  Gly  Gln  Val  Arg  Tyr  Ile  Glu  Tyr  Met  Phe  Arg  Thr  Gly  Cys
               725                      730                      735
```

| | | | | | | | | | | | | | | |
|---|---|---|---|---|---|---|---|---|---|---|---|---|---|---|
| Glu | Trp | Ser | Pro 740 | Cys | Ser | Thr | Gln | Leu 745 | Ala | Cys | Glu | Val | Gly 750 | Val | Gln |
| Ser | Arg | Ser 755 | Arg | Gln | Cys | Val | Gly 760 | Glu | Ser | Gly | Cys | His 765 | Cys | Ile | Gly |
| Leu | Ala | Glu 770 | Glu | Ser | Gln | Gln 775 | Cys | Arg | Gly | Leu | Thr 780 | Gln | Cys | Pro | Pro |
| Lys 785 | Pro | Pro | Cys | | | | | | | | | | | | |

HUMAN NUCLEOTIDE PYROPHOSPHOHYDROLASE

FIELD OF THE INVENTION

This invention relates to nucleic acid and amino acid sequences of a human nucleotide pyrophosphohydrolase and to the use of these sequences in the diagnosis, prevention, and treatment of arthropathies, immunological disorders, and cancers.

BACKGROUND

Calcium pyrophosphate dihydrate (CPPD) deposition disease is an arthropathy characterized by the accumulation of CPPD crystals in articular tissues including synovial fluid. CPPD crystals contribute significantly to the chronic pain and tissue damage of joint degeneration, and they induce neutrophil activation, fibroblast and chondrocyte mitogenesis and production of MMP and prostaglandins in vitro. CPPD deposition is associated with acute inflammatory attacks (pseudogout), chronic arthritis, and degenerative joint disease. Although only about 10% of the CPPD patient population ever experiences acute inflammatory attacks, the majority of patients with chronic arthritis of the large joints have CPPD deposition. CPPD crystals play a significant role in arthritic disease progression. The synovial fluids sampled from patients with degenerative joint disease contain CPPD crystals, cartilage fragments, and matrix metalloproteinases (MMP) such as collagenase and stromelysin. (Swan, A. B. et al. (1994) Ann. Rheum. Dis. 53:467–470; Lohmander, L. S. et al. (1993) Arthritis. Rheum. 36:181–189).

Deposition of CPPD crystals appears to be related to excess levels of extracellular calcium, pyrophosphate (PPi), or both. Whereas elevated calcium levels do not appear to be a major contributing factor to CPPD deposition in joints, elevated PPi levels have been noted in the synovial fluids from patients with CPPD deposition. Synovial fluid PPi seems to be produced by joint tissues since PPi levels are higher in the synovial fluid than in the plasma. The fact that in vitro cartilage explants release PPi into the extracellular medium also suggests that cartilage is a primary source of PPi (Ryan, L. M. et al. (1996) J. Rheumatol. 23:214–219).

Enzymes that hydrolyze nucleotide triphosphates and release PPi are called nucleotide pyrophosphohydrolases (NTPPH). NTPPH activity is found in synovial fluid and correlates with the production of PPi. Elevated ATP levels have been found in joint fluids of patients with CPPD deposition, and addition of extracellular ATP to joint tissues and fluids results in the production of PPi (Park, W. I. et al. (1996) J. Rheumatol. 23:665–671). Molecules exhibiting NTPPH activity can be extracted from cartilage using detergent, and the levels of molecules demonstrating NTPPH activity are higher in extracts from cartilage containing CPPD crystals than from cartilage lacking crystals. Matrix vesicles released from articular cartilage show high NTPPH activity and generate CPPD in vitro in the presence of calcium and ATP (Derfus, B. A. et al. (1992) Arthritis. Rheum. 35:231–240).

A protein demonstrating NTPPH and having a molecular weight of 61 kD activity was recently obtained from medium conditioned with porcine articular cartilage explant. The first 26 residues of the amino-terminal sequence were determined and showed no homology to any protein in public databases. Antipeptide antibodies were generated against the 61 kD porcine protein, and the antisera identified the original 61 kD protein and an additional 127 kD vesicle-associated protein in conditioned medium from cultures of both chondrocytes and cartilage explants. The 61 kD isoform is believed to be a catalytically active proteolytic fragment of the 127 kD protein. Both the 61 kD and the 127 kD isoforms were identified in human synovial fluids, and a 100 kD protein was identified in human serum. Using the antipeptide antibody on immunoblots of tissue extracts, NTPPH expression was found to be restricted to the articular tissues in which CPPD deposition occurs: hyaline cartilage, fibrocartilage, tendon, and ligament (Cardenal, A. et al. (1996) Arthritis Rheum. 39:252–256; Cardenal, A. et al. (1996) Arthritis Rheum. 39:245–251).

The discovery of a new human nucleotide pyrophosphohydrolase and the polynucleotides encoding it satisfies a need in the art by providing new compositions which are useful in the diagnosis, prevention and treatment of arthropathies, immunological disorders, and cancers.

SUMMARY OF THE INVENTION

The invention features a substantially purified polypeptide, human nucleotide pyrophosphohydrolase (NTPPH-1), having the amino acid sequence shown in SEQ ID NO:1, or fragments thereof.

The invention further provides an isolated and substantially purified polynucleotide sequence encoding the polypeptide comprising the amino acid sequence of SEQ ID NO:1 or fragments thereof and a composition comprising said polynucleotide sequence. The invention also provides a polynucleotide sequence which hybridizes under stringent conditions to the polynucleotide sequence encoding the amino acid sequence SEQ ID NO:1, or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO:2 or variants thereof. In addition, the invention provides a polynucleotide sequence which hybridizes under stringent conditions to the polynucleotide sequence of SEQ ID NO:2. The invention also provides a polynucleotide sequence comprising the complement of SEQ ID NO:2, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding NTPPH-1 under conditions suitable for the expression of the polypeptide; and b) recovering the polypeptide from the host cell culture.

The invention also provides a pharmaceutical composition comprising a substantially purified NTPPH-1 having the amino acid sequence of SEQ ID NO:1 in conjunction with a suitable pharmaceutical carrier.

The invention also provides a purified antagonist of the polypeptide of SEQ ID NO:1. In one aspect the invention provides a purified antibody which binds to a polypeptide comprising the amino acid sequence of SEQ ID NO:1.

Still further, the invention provides a purified agonist of the polypeptide of SEQ ID NO:1.

The invention also provides a method for treating or preventing an arthropathy, comprising administering to a subject in need of such treatment an effective amount of an antagonist of NTPPH-1.

The invention also provides a method for treating or preventing an immunological disorder comprising administering to a subject in need of such treatment an effective amount of an antagonist of NTPPH-1.

The invention also provides a method for treating or preventing a cancer comprising administering to a subject in need of such treatment an effective amount of an antagonist of NTPPH-1.

The invention also provides a method for detecting a polynucleotide which encodes NTPPH-1 in a biological sample comprising the steps of: a) hybridizing the complement of the polynucleotide sequence which encodes SEQ ID NO:1 to nucleic acid material of a biological sample, thereby forming a hybridization complex; and b) detecting the hybridization complex, wherein the presence of the complex correlates with the presence of a polynucleotide encoding NTPPH-1 in the biological sample. In one aspect the nucleic acid material of the biological sample is amplified by the polymerase chain reaction prior to hybridization.

The invention also provides a method for detecting NTPPH-1 in a biological sample comprising the steps of: a) providing a biological sample, b) combining the biological sample and an anti-NTPPH-1 antibody, c) allowing complex formation to occur between NTPPH-1 and the antibody, and d) detecting complex formation, thereby establishing the presence of NTPPH-1 in the biological sample.

BRIEF DESCRIPTION OF THE FIGURES

FIGS. 1A, 1B, 1C, 1D, 1E, 1F, 1G, 1H and 1I show the amino acid sequence (SEQ ID NO:1) and nucleic acid sequence (SEQ ID NO:2) of human nucleotide pyrophosphohydralase, NTPPH-1. The alignment was produced using MACDNASIS software (Hitachi Software Engineering Co. Ltd. San Bruno, Calif.).

FIGS. 2A, 2B, and 2C show sequence alignments between NTPPH-1 and deduced protein of an NCBI EST (GI 1515673; SEQ ID NO:3), and between NTPPH-1 and a *Caenorhabditis elegans* protein, T21B6.3 (GI 1070094; SEQ ID NO:6).

FIG. 5 shows an electronic northern analysis for NTPPH-1, produced using LIFESEQ database (Incyte Pharmaceuticals, Inc. Palo Alto, Calif.).

DESCRIPTION OF THE INVENTION

Figure 3:
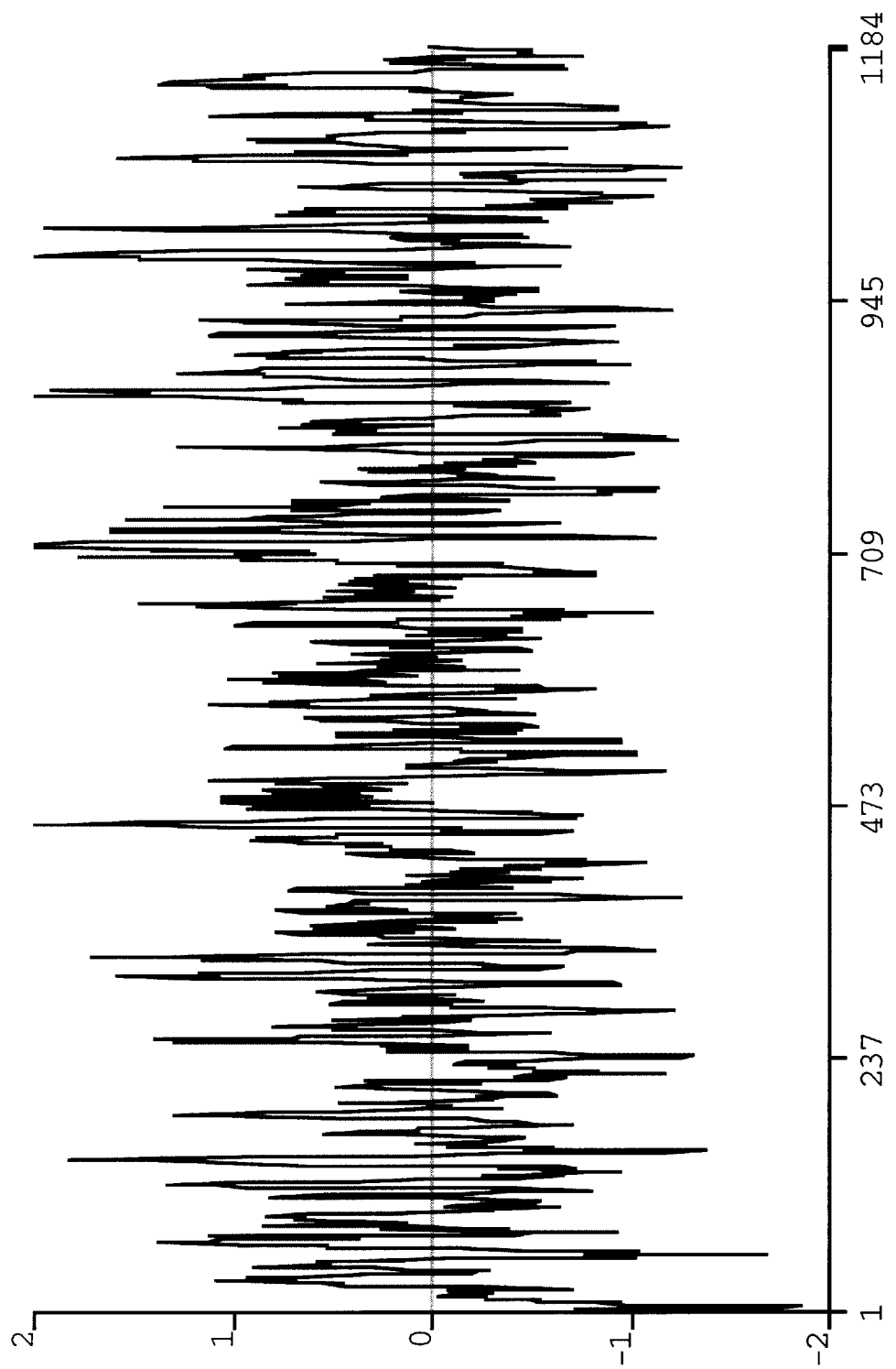
FIG. 3 shows a hydrophobicity plot for NTPPH-1 (SEQ ID NO: 1); The positive X axis reflects amino acid position, and the negative Y axis hydrophobicity (MACDNASIS PRO software).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

NTPPH-1, as used herein, refers to the amino acid sequences of substantially purified nucleotide pyrophosphohydrolase obtained from any species, particularly mammalian, including bovine, ovine, murine, and equine, and preferably human, from any source whether natural, synthetic, semi-synthetic, or recombinant.

The term "agonist", as used herein, refers to a molecule which, when bound to NTPPH-1, increases or prolongs the duration of the effect of NTPPH-1. Agonists may include proteins, nucleic acids, carbohydrates, or any other molecules which bind to and modulate the effect of NTPPH-1.

An "allele" or "allelic sequence", as used herein, is an alternative form of the gene encoding NTPPH-1. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding NTPPH-1 as used herein include those with deletions, insertions, or substitutions of different nucleotides resulting in a polynucleotide that encodes the same or a functionally equivalent NTPPH-1. Included within this definition are polymorphisms which may or may not be readily detectable using a particular oligonucleotide probe of the polynucleotide encoding NTPPH-1, and improper or unexpected hybridization to alleles, with a locus other than the normal chromosomal locus for the polynucleotide sequence encoding NTPPH-1. The encoded protein may also be "altered" and contain deletions, insertions, or substitutions of amino acid residues which produce a silent change and result in a functionally equivalent NTPPH-1. Deliberate amino acid substitutions may be made on the basis of similarity in polarity, charge, solubility, hydrophobicity, hydrophilicity, and/or the amphipathic nature of the residues as long as the biological or immunological activity of NTPPH-1 is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of NTPPH-1 are preferably about 5 to about 15 amino acids in length and retain the biological activity or the immunological activity of NTPPH-1. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C W and G S Dveksler (1995) *PCR Primer, a Laboratory Manual*, Cold Spring Harbor Press, Plainview, N.Y.).

The term "antagonist" as used herein, refers to a molecule which, when bound to NTPPH-1, decreases the amount or the duration of the effect of the biological or immunological activity of NTPPH-1. Antagonists may include proteins, nucleic acids, carbohydrates, antibodies or any other molecules which decrease the effect of NTPPH-1.

As used herein, the term "antibody" refers to intact molecules as well as fragments thereof, such as Fab, F(ab')$_2$, and Fv, which are capable of binding the epitopic determinant. Antibodies that bind NTPPH-1 polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic NTPPH-1, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing.

For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding NTPPH-1 (SEQ ID NO:1) or fragments thereof (e.g., SEQ ID NO:2 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW fragment assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2 by northern analysis is indicative of the presence of mRNA encoding NTPPH-1 in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to NTPPH-1 or the encoded NTPPH-1. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of NTPPH-1. For example, modulation may cause an increase or a decrease in protein activity, binding characteristics, or any other biological, functional or immunological properties of NTPPH-1.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray.

As used herein, oligonucleotide is substantially equivalent to the terms "amplimers","primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1" encompasses the full-length NTPPH-1 and fragments thereof.

The term "sample", as used herein, is used in its broadest sense. A biological sample suspected of containing nucleic acid encoding NTPPH-1, or fragments thereof, or NTPPH-1 itself may comprise a bodily fluid, extract from a cell, chromosome, organelle, or membrane isolated from a cell, a cell, genomic DNA, RNA, or cDNA(in solution or bound to a solid support, a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions"or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of NTPPH-1, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of a new human nucleotide pyrophosphohydrolase, hereinafter referred to as "NTPPH-1", the polynucleotides encoding NTPPH-1, and the use of these compositions for the diagnosis, prevention, or treatment of arthropathies, immunological disorders, and cancers.

Nucleic acids encoding a portion of the NTPPH-1 of the present invention were first identified in Incyte Clone 422069 from an IL-1 stimulated osteoarthritic chondrocyte cDNA library (SATPF1002) using a computer search for nucleotide sequence alignments. Incyte Clone 422069 and the SATPF008 and SATPF010 chondrocyte libraries were used to produce SEQ ID NO:2.

Figure 4:
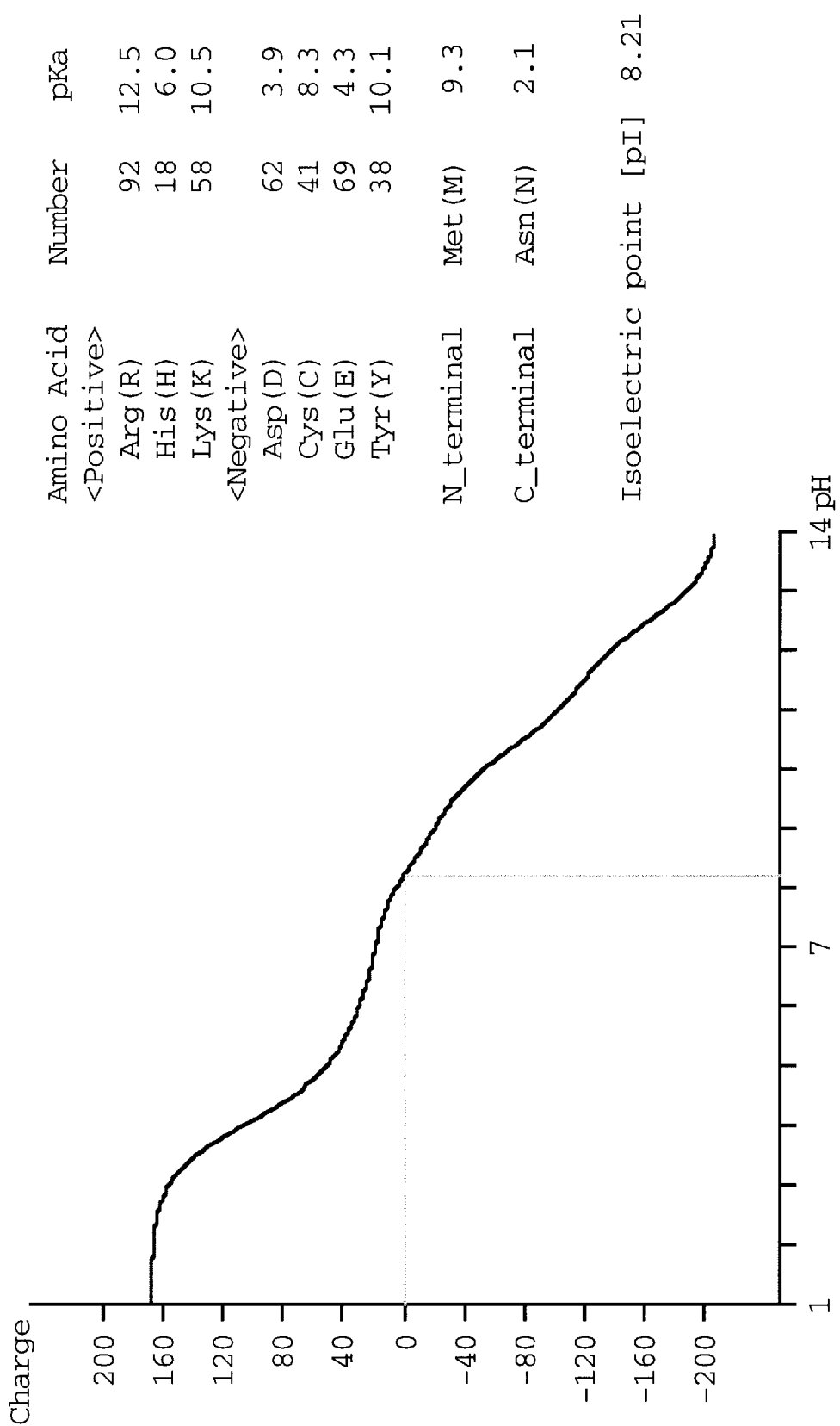
FIG. 4 shows an isoelectric plot for NTPPH-1 (SEQ ID NO: 1; MACDNASIS PRO software).

In one embodiment, the invention encompasses a polypeptide comprising the amino acid sequence of SEQ ID NO:1, as shown in FIGS. 1A, 1B, 1C, 1D, 1E, 1F, 1G, 1H, and 1I. NTPPH-1 is 1184 amino acids in length and has eight potential N glycosylation sites at residues N129, N132, N346, N420, N550, N631, N1000, and N1056; 38 potential phosphorylation sites at S29, S52, S112, T134, S143, T148, T201, T249, T254, T256, S293, T298, T333, T348, S458, S497, T534, T540,T551, S562, T625, T695, S749, S761, S839, T862, S885, S936, T976, S992, S1032, T1037,T1078, T1080, T1086, S1103, S1152, and S1171; one potential aldehyde dehydrogenase active site, $A_{188}$SEEGQHCMGQD$_{199}$; and one ATP/GTP-binding site motif A, $G_{266}$LCPDGK$_{272}$. As shown in FIGS. 2A, 2B and 2C, NTPPH-1 has chemical and structural homology with an NCBI EST (GI 1515673; SEQ ID NO:3) and with a $C.$ $elegans$, protein T21B6.3 (GI 1070094; SEQ ID NO:6). The hydrophobicity and isoelectric plots for NTPPH-1 are shown in FIGS. 3 and 4, respectively. Membrane-based northern analyses of human, dog and rabbit joint tissue RNA samples demonstrated the highest level of NTPPH-1 expression in articular cartilage and lower, but significant, expression in synovium, meniscus, tendon and ligament. Expression studies on additional human tissues demonstrated significant mRNA levels in skeletal muscle, heart muscle and bone marrow; and lower, but detectable, levels in trachea, spinal cord, thyroid, stomach, testis, uterus, small intestine, colon, thymus, placenta, lymph and adrenal tissue. Electronic northern analysis using the LIFESEQ database (FIG. 5) showed the expression of NTPPH-1 in various libraries, at least 44% of which are immortalized or cancerous and at least 25% of which involve immune response. Of particular note is the expression of NTPPH-1 in tissues of the gastrointestinal system (17%), reproductive system (13%), cardiovascular system (13%), and synovia (6%).

The invention also encompasses NTPPH-1 variants. A preferred NTPPH-1 variant is one having at least 80%, and more preferably at least 90%, amino acid sequence identity to the NTPPH-1 amino acid sequence (SEQ ID NO:1) and which retains at least one biological, immunological or other functional characteristic or activity of NTPPH-1. A most preferred NTPPH-1 variant is one having at least 95% amino acid sequence identity to SEQ ID NO:1.

The invention also encompasses polynucleotides which encode NTPPH-1. Accordingly, any nucleic acid sequence which encodes the amino acid sequence of NTPPH-1 can be used to produce recombinant molecules which express NTPPH-1. In a particular embodiment, the invention encompasses the polynucleotide comprising the nucleic acid sequence of SEQ ID NO:2 as shown in FIGS. 1A, 1B, 1C, 1D, 1E, 1F, 1G, 1H and 1I.

It will be appreciated by those skilled in the art that as a result of the degeneracy of the genetic code, a multitude of nucleotide sequences encoding NTPPH-1, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring NTPPH-1, and all such variations are to be considered as being specifically disclosed.

Although nucleotide sequences which encode NTPPH-1 and its variants are preferably capable of hybridizing to the nucleotide sequence of the naturally occurring NTPPH-1 under appropriately selected conditions of stringency, it may be advantageous to produce nucleotide sequences encoding NTPPH-1 or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding NTPPH-1 and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode NTPPH-1 and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding NTPPH-1 or any fragment thereof.

Also encompassed by the invention are polynucleotide sequences that are capable of hybridizing to the claimed nucleotide sequences, and in particular, those shown in SEQ ID NO:2, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE amplification system marketed by GIBCO/BRL(Gaithersburg, Md.). Preferably, the process is automated with machines such as the Hamilton MICRO LAB 2200 (Hamilton, Reno, N.V.), Peltier thermal cycler (PTC200; MJ Research, Watertown, Mass.) and the ABI Catalyst and 373 and 377 DNA SEQUENCERS (Perkin Elmer).

The nucleic acid sequences encoding NTPPH-1 may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode NTPPH-1 may be used in recombinant DNA molecules to direct expression of NTPPH-1, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express NTPPH-1.

As will be understood by those of skill in the art, it may be advantageous to produce NTPPH-1-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter NTPPH-1 encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding NTPPH-1 may be ligated to a heterologous sequence to encode a fusion protein. For example, to screen peptide libraries for inhibitors of NTPPH-1 activity, it may be useful to encode a chimeric NTPPH-1 protein that can be recognized by a commercially available antibody. A fusion protein may also be engineered to contain a cleavage site located between the NTPPH-1 encoding sequence and the heterologous protein sequence, so that NTPPH-1 may be cleaved and purified away from the heterologous moiety.

In another embodiment, sequences encoding NTPPH-1 may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of NTPPH-1, or a fragment thereof. For example, peptide synthesis can be performed using various solid-phase techniques (Roberge, J. Y. et al. (1995) Science 269:202–204) and automated synthesis may be achieved, for example, using the Applied Biosystems 431A peptide synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of NTPPH-1, or any part thereof, may be altered during direct synthesis and/or combined using chemical methods with sequences from other proteins, or any part thereof, to produce a variant polypeptide.

In order to express a biologically active NTPPH-1, the nucleotide sequences encoding NTPPH-1 or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding NTPPH-1 and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding NTPPH-1. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT 1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding NTPPH-1, vectors based on SV40 or EBV may be used with an appropriate selectable marker.

In bacterial systems, a number of expression vectors may be selected depending upon the use intended for NTPPH-1. For example, when large quantities of NTPPH-1 are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding NTPPH-1 may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding NTPPH-1 may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, flobbs, S. or Murry, L. E. in McGraw Hill *Yearbook of Science and Technology* (1992) McGraw Hill, New York, N.Y.; pp. 191–196.

An insect system may also be used to express NTPPH-1. For example, in one such system, *Autographa californica* nuclear polyhedrosis virus (AcNPV) is used as a vector to express foreign genes in *Spodoptera frugiperda* cells or in Trichoplusia larvae. The sequences encoding NTPPH-1 may be cloned into a non-essential region of the virus, such as the polyhedrin gene, and placed under control of the polyhedrin promoter. Successful insertion of NTPPH-1 will render the polyhedrin gene inactive and produce recombinant virus lacking coat protein. The recombinant viruses may then be used to infect, for example, *S. frugiperda* cells or Trichoplusia larvae in which NTPPH-1 may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding NTPPH-1 may be ligated into an adenovirus transcription/translation complex consisting of the late promoter and tripartite leader sequence. Insertion in a non-essential E1 or E3 region of the viral genome may be used to obtain a viable virus which is capable of expressing NTPPH-1 in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding NTPPH-1. Such signals include the ATG initiation codon and adjacent sequences. In cases where sequences encoding NTPPH-1, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express NTPPH-1 may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk$^-$ or aprt$^-$ cells, respectively. Also, antimetabolite, antibiotic or herbicide resistance can be used as the basis for selection; for example, dhfr, which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding NTPPH-1 is inserted within a marker gene sequence, transformed cells containing sequences encoding NTPPH-1 can be identified by the absence of marker gene function. Alternatively, a marker gene can be placed in tandem with a sequence encoding NTPPI-1 under the control of a single promoter. Expression of the marker gene in response to induction or selection usually indicates expression of the tandem gene as well.

Alternatively, host cells which contain the nucleic acid sequence encoding NTPPH-1 and express NTPPH-1 may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of nucleic acid or protein.

The presence of polynucleotide sequences encoding NTPPH-1 can be detected by DNA—DNA or DNA-RNA hybridization or amplification using probes or fragments or fragments of polynucleotides encoding NTPPH-1. Nucleic acid amplification based assays involve the use of oligonucleotides or oligomers based on the sequences encoding NTPPH-1 to detect transformants containing DNA or RNA encoding NTPPH-1.

A variety of protocols for detecting and measuring the expression of NTPPH-1, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on NTPPH-1 is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding NTPPH-1 include oligolabeling, nick translation, end-labeling or PCR amplification using a labeled nucleotide. Alternatively, the sequences encoding NTPPH-1, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., (Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding NTPPH-1 may be cultured under conditions suitable for the expression and recovery of the protein from cell culture. The protein produced by a transformed cell may be secreted or contained intracellularly depending on the sequence and/ or the vector used. As will be understood by those of skill in the art, expression vectors containing polynucleotides which encode NTPPH-1 may be designed to contain signal sequences which direct secretion of NTPPH-1 through a prokaryotic or eukaryotic cell membrane. Other constructions may be used to join sequences encoding NTPPH-1 to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and NTPPH-1 may be used to facilitate purification. One such expression vector provides for expression of a fusion protein containing NTPPH-1 and a nucleic acid encoding 6 histidine residues preceding a thioredoxin or an enterokinase cleavage site. The histidine residues facilitate purification on IMAC (immobilized metal ion affinity chromatography as described in Porath, J. et al. (1992, Prot. Exp. Purif. 3: 263–281) while the enterokinase cleavage site provides a means for purifying NTPPH-1 from the fusion protein. A discussion of vectors which contain fusion proteins is provided in Kroll, D. J. et al. (1993; DNA Cell Biol. 12:441–453).

In addition to recombinant production, fragments of NTPPH-1 may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using an Applied Biosystems 431A peptide synthesizer (Perkin Elmer). Various fragments of NTPPH-1 may be chemically synthesized separately and combined using chemical methods to produce the full length molecule.

THERAPEUTICS

Chemical and structural homology exists among NTPPH-1, three NCBI ESTs (GI 1515673, GI 1131415, and GI 2015160), and a *Caenorhabditis elegans* protein, T21B6.3 (GI 1070094; SEQ ID NO:4). Transcripts encoding NTPPH-1 were expressed in cartilage, joint and skeletal muscle, uterus, breast, brain, intestine, and tumor libraries. Electronic northern analysis (FIG. 5) showed expression of NTPPH-1 in tissues of the gastrointestinal system (17%), reproductive system (13%), cardiovascular system (13%), and synovia (6%). Therefore, NTPPH-1 appears to play a role in arthropathies, immunological disorders, and cancers.

Therefore, in one embodiment, an antagonist of NTPPH-1 may be administered to a subject to prevent or treat an arthropathy. Arthropathies include, but are not limited to, Behcet's syndrome, Charcot osteoarthropathy, CPPD disease, diabetic neuropathic arthropathy, degenerative joint disease, fibromyalgias, hemachromatosis, hemophilic arthropathy, Jaccoud's type arthropathy, lupus erythematosus, mixed connective tissue disease, Muckle-Wells syndrome, osteoarthritis, progressive systemic sclerosis, pseudogout, psoriasis, Reiter's syndrome, rheumatoid arthritis, Sjögren's syndrome, spondyloarthropathies, and ulcerative colitis. In one aspect, an antibody which specifically binds NTPPH-1 may be used directly as an antagonist or indirectly as a targeting or delivery mechanism for bringing a pharmaceutical agent to cells or tissue which express NTPPH-1.

In another embodiment, a vector expressing the complement of the polynucleotide encoding NTPPH-1 may be administered to a subject to treat or prevent an arthropathy including, but not limited to, those described above.

In another embodiment, an antagonist of NTPPH-1 may be administered to a subject to prevent or treat an immunological disorder. Immunological disorders include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, multiple sclerosis, myasthenia gravis, myocardial or pericardial inflammation, osteoporosis, pancreatitis, polymyositis, scleroderma, and autoimmune thyroiditis; complications of cancer, hemodialysis, and extracorporeal circulation; viral, bacterial, fungal, to parasitic, protozoal, and helminthic infections; and trauma. Such disorders may be characterized by the production of cytokines and the multiplication of leukocytes, macrophages, and other cells which may cause tissue damage. In one aspect, an antibody which specifically binds NTPPH-1 may be used directly as an antagonist or indirectly as a targeting or delivery mechanism for bringing a pharmaceutical agent to cells or tissue which express NTPPH-1.

In another embodiment, a vector expressing the complement of the polynucleotide encoding NTPPH-1 may be administered to a subject to treat or prevent an immunological disorder including, but not limited to, those described above.

In another embodiment, an antagonist of NTPPH-1 may be administered to a subject to prevent or treat a cancer. Cancers include adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds NTPPH-1 may be used directly as an antagonist or indirectly as a targeting or delivery mechanism for bringing a pharmaceutical agent to cells or tissue which express NTPPH-1.

In another embodiment, a vector expressing the complement of the polynucleotide encoding NTPPH-1 may be administered to a subject to treat or prevent a cancer including, but not limited to, those described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of NTPPH-1 may be produced using methods which are generally known in the art. In particular, purified NTPPH-1 may be used to produce antibodies or to screen libraries of pharmaceutical agents to identify those which specifically bind NTPPH-1.

Antibodies to NTPPH-1 may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit enzymatic activity) are especially preferred for therapeutic use.

For the production of antibodies, various hosts including goats, rabbits, rats, mice, humans, and others, may be immunized by injection with NTPPH-1 or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to NTPPH-1 have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of NTPPH-1 amino acids may be fused with those of another protein such as keyhole limpet hemocyanin and antibody produced against the chimeric molecule.

Monoclonal antibodies to NTPPH-1 may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce NTPPH-1-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for NTPPH-1 may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between NTPPH-1 and its specific antibody. A two-site, monoclonal-based immunoassay utilizing monoclonal antibodies reactive to two non-interfering NTPPH-1 epitopes is preferred, but a competitive binding assay may also be employed (Maddox, supra).

In another embodiment of the invention, the polynucleotides encoding NTPPH-1, or any fragment or complement thereof, may be used for therapeutic purposes. In one aspect, the complement of the polynucleotide encoding NTPPH-1 may be used in situations in which it would be desirable to block the transcription of the mRNA. In particular, cells may be transformed with sequences complementary to polynucleotides encoding NTPPH-1. Thus, complementary molecules or fragments may be used to modulate NTPPH1 activity, or to achieve regulation of gene function. Such technology is now well known in the art, and sense or antisense oligonucleotides or larger fragments, can be designed from various locations along the coding or control regions of sequences encoding NTPPH-1.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding NTPPH-1. These techniques are described both in Sambrook et al. (supra) and in Ausubel et al. (supra).

Genes encoding NTPPH-1 can be turned off by transforming a cell or tissue with expression vectors which express high levels of a polynucleotide or fragment thereof which encodes NTPPH-1. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding NTPPH-1 (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding NTPPH-1.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding NTPPH-1. Such DNA sequences may be incorporated into a wide variety of vectors with suitable RNA polymerase promoters such as T7 or SP6.Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of NTPPH-1, antibodies to NTPPH-1, mimetics, agonists, antagonists, or inhibitors of NTPPH-1. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, car-bopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicle include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of NTPPH-1, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example NTPPH-1 or fragments thereof, antibodies of NTPPH-1, agonists, antagonists or inhibitors of NTPPH-1, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, which can be expressed as the ratio LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind NTPPH-1 may be used for the diagnosis of conditions or diseases characterized by expression of NTPPH-1, or in assays to monitor patients being treated with NTPPH-1, agonists, antagonists or inhibitors. The antibodies useful for diagnostic purposes may be prepared in the same manner as those described above for therapeutics. Diagnostic assays for NTPPH-1 include methods which utilize the antibody and a label to detect NTPPH-1 in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring NTPPH-1 are known in the art and provide a basis for diagnosing altered or abnormal levels of NTPPH-1 expression. Normal or standard values for NTPPH-1 expression are established by combining body fluids or cell extracts taken from normal mammalian subjects, preferably human, with antibody to NTPPH-1 under conditions suitable for complex formation The amount of standard complex formation may be quantified by various methods, but preferably by photometric, means. Quantities of NTPPH-1 expressed in subject, control and disease, samples from biopsied tissues are compared with the standard values. Deviation between standard and subject values establishes the parameters for diagnosing disease.

In another embodiment of the invention, the polynucleotides encoding NTPPH-1 may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of NTPPH-1 may be correlated with disease. The diagnostic assay may be used to distinguish between absence, presence, and excess expression of NTPPH-1, and to monitor regulation of NTPPH-1 levels during therapeutic intervention.

In one aspect, hybridization with PCR probes which are capable of detecting polynucleotide sequences, including genomic sequences, encoding NTPPH-1 or closely related molecules, may be used to identify nucleic acid sequences which encode NTPPH-1. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding NTPPH-1, alleles, or related sequences.

Probes may also be used for the detection of related sequences, and should preferably contain at least 50% of the nucleotides from any of the NTPPH-1 encoding sequences. The hybridization probes of the subject invention may be DNA or RNA and derived from the nucleotide sequence of SEQ ID NO:2 or from genomic sequence including promoter, enhancer elements, and introns of the naturally occurring NTPPH-1.

Means for producing specific hybridization probes for DNAs encoding NTPPH-1 include the cloning of nucleic acid sequences encoding NTPPH-1 or NTPPH-1 derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding NTPPH-1 may be used for the diagnosis of conditions or disorders which are associated with expression of NTPPH-1. Examples of such conditions or disorders include, but are not limited to, the following: 1) arthropathies including, Behcet's syndrome. Charcot osteoarthropathy, CPPD disease, diabetic neuropathic arthropathy, degenerative joint disease, fibromyalgias, hemachromatosis, hemophilic arthropathy, Jaccoud's type arthropathy, lupus erythematosus, mixed connective tissue disease, Muckle-Wells syndrome, osteoarthritis, progressive systemic sclerosis, pseudogout, psoriasis, Reiter's syndrome, rheumatoid arthritis, Sjögren's syndrome, spondyloarthropathies, and ulcerative colitis; 2) immunological disorders including, but not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, multiple sclerosis, myasthenia gravis, myocardial or pericardial inflammation, osteoporosis, pancreatitis, polymyositis, scleroderma, and autoimmune thyroiditis; complications of cancer, hemodialysis, and extracorporeal circulation; viral, bacterial, fungal, parasitic, protozoal, and helminthic infections; and trauma; and 3) cancers including, adenocarcinoma, leukemia, lymphoma, melanoma, myeloma, sarcoma, teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

The polynucleotide sequences encoding NTPPH-1 may be used in Southern or northern analysis, dot blot, or other membrane-based technologies; in PCR technologies; or in dipstick, pin, ELISA assays or microarrays utilizing fluids or tissues from patient biopsies to detect altered NTPPH-1 expression. Such qualitative or quantitative methods are well known in the art.

In a particular aspect, the nucleotide sequences encoding NTPPH-1 may be useful in assays that detect activation or induction of various cancers, particularly those mentioned above. The nucleotide sequences encoding NTPPH-1 may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding NTPPH-1 in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of NTPPH-1, a normal or standard profile for expression is established. This may be accomplished by combining body fluids or cell extracts taken from normal subjects, either animal or human, with a sequence, or a fragment thereof, which encodes NTPPH-1, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding NTPPH-1 may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of NTPPH-1 include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 212:229–236. The speed of quantitation of multiple samples may be accelerated by running the assay in an ELISA format where the oligomer of interest is presented in various dilutions and a spectrophotometric or colorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode NTPPH-1 may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding NTPPH-1 on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, NTPPH-1, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between NTPPH-1 and the agent being tested, may be measured.

Another technique for drug screening which may be used provides for high throughput screening of compounds having suitable binding affinity to the protein of interest as described in published PCT application WO84/03564. In this method, as applied to NTPPH-1 large numbers of different small test compounds are synthesized on a solid substrate, such as plastic pins or some other surface. The test compounds are reacted with NTPPH-1, or fragments thereof, and washed. Bound NTPPH-1 is then detected by methods well known in the art. Purified NTPPH-1 can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding NTPPH-1 specifically compete with a test compound for binding NTPPH-1. In this manner, the antibodies can be used to detect the presence of any peptide which shares one or more antigenic determinants with NTPPH-1.

In additional embodiments, the nucleotide sequences which encode NTPPH-1 may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I SATPF1002 OA Cartilage cDNA Library

The SATPF1002 cDNA library was constructed from the pooled RNAs extracted from four cartilage samples surgically removed from the knees of two males, ages 48 and 82 years, and two females, ages 57 and 64 years, with osteoarthritis. These primary arthritis patients had all been treated with steroids such as prednisone or non-steroidal anti-inflammatory drugs such as aspirin, acetominophen, ibuprofen, motrin etc. The tissue was harvested and placed in Dulbecco's Modified Eagle Medium (D-MEM; Gibco/BRL) supplemented with antibiotics (penicillin, streptomycin, and gentamicin) and transported to Pfizer laboratories in Groton Conn. The cartilage was removed aseptically from the underlying bone, rinsed in D-MEM and diced into small pieces (~4 mm$^2$), and placed in 100 mm petri dishes containing 20 ml of Neuman and Tytell's serum free medium (GIBCO/BRL). Interleukin -1a, at a concentration of 5 ng/ml, was added to the media, and the cartilage was incubated for approximately 18 hours at 37° C. to induce the over-expression of genes such as the metalloproteinases. Using the protocol of Cathala G et al (1983; DNA 2:329–335), the cartilage from each patient was digested with 4 mg/ml pronase (Sigma, St Louis) for 1.5 hours, then subsequently digested with 3 mg/ml bacterial collagenase (Sigma) for 1.5 hours. The digested material was filtered through a cell strainer, and the cells were pelleted by centrifugation. The cell pellet was washed once with phosphate buffered saline and then dissolved in 5 ml of buffer consisting of 5M guanidine isothiocyanate, 10 mM EDTA, 50 mM Tris (pH 7.5) and 8% β mercaptoethanol. A five-fold volume of 4M LiCl was added to the buffer, and the mixture was stored in the refrigerator overnight. After centrifugation, the precipitate was washed once with 3M LiCl and recentrifuged. The second precipitate was dissolved in a solution consisting of 0.1% sodium dodecyl sulfate, 1 mM EDTA and 10 mM Tris (pH 7.5). The suspension was frozen at −70° C. and then vortexed during thawing.

Total RNA was extracted twice with phenol chloroform, once with chloroform, and then, precipitated with ethanol. Following centrifugation, the RNA pellet was redissolved in DEPC treated, distilled deionized water (DEPC-ddHOH) and run over a CsCl gradient. The RNA was extracted with acid phenol (1× at pH 4.0, catalog #972Z, Ambion, Austin Tex.), precipitated with ethanol and resuspended in DEPC-ddHOH. The RNA was treated with RNAse-free DNAse (Epicentre Technologies, Madison Wis.) for 15 minutes, extracted with chloroform, precipitated and washed with ethanol, and dissolved in DEPC-ddHOH. Since the RNA yield varied with each sample, approximately 40% of total RNA from each sample was contributed to the pooled sample.

The pooled RNA was used to construct a custom cDNA library. The RNA was handled according to the recommended protocols in the SUPERSCRIPT plasmid system for cDNA synthesis and plasmid cloning (catalog #18248-013; GIBCO/BRL). Those cDNAs exceeding 400 bp were ligated into the vector, PSPORT 1, and the plasmid was subsequently transformed into DH5a competent cells (Cat. #18258-012, GIBCO/BRL).

II Isolation and Sequencing of cDNA Clones

Plasmid DNA was purified using the Miniprep Kit (catalog # 77468, Advanced Genetic Technologies Corporation, Gaithersburg Md.), a 96-well block kit with reagents for 960 purifications. The recommended protocol included with the kit was employed except for the following changes. Each of the 96 wells was filled with only 1 ml of sterile Terrific Broth (Catalog # 22711, GIBCO/BRL) with carbenicillin at 25 mg/L and glycerol at 0.4%. After the wells were inoculated, the bacteria were cultured for 24 hours and lysed with 60 μl of lysis buffer. A centrifugation step (Beckman GS-6R @2900 rpm for 5 min; Beckman Instruments) was performed before the contents of the block were added to the primary filter plate. The optional step of adding isopropanol to TRIS buffer was not routinely performed. After the last step in the protocol, samples were transferred to a Beckman 96-well block for storage.

The cDNAs were sequenced by the method of Sanger F and AR Coulson (1975; J Mol Biol 94:441f), using a Hamilton MICROLAB 2200 (Hamilton, Reno N.V.) in combination with four Peltier thermal cyclers (PTC200 from MJ Research, Watertown Mass.) and Applied Biosystems 377 or 373 DNA sequencing systems (Perkin Elmer), and reading frame was determined.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Toot (Altschul SF (1993) J Mol Evol 36:290–300; Altschul, SF ct al (1990) J Mol Biot 215:403–10).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith RF and TF Smith (1992 Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin and Altschul (1993; Proc Nat Acad Sci 90:5873–7) and incorporated herein by reference, searches matches between a query sequence and a database sequence, to evaluate the statistical significance of any matches found, and to report only those matches which satisfy the user-selected threshold of significance. In this application, threshold was set at 10–25 for nucleotides and 10–14 for peptides.

Incyte nucleotide sequence were searched against the GenBank databases for pri=primate, rod=rodent, and mam= mammalian sequences, and deduced amino acid sequences from the same clones are searched against GenBank functional protein databases, mamp=mammalian, vrtp= vertebrate and eukp=eukaryote, for homology.

IV Cloning and sequencing of the cDNAs encoding NTPPH-1

Dr. L. M. Ryan (Medical College of Wisconsin, Milwaukee, Wis.) provided a 2.3 kb unpublished cDNA sequence which encodes a partial porcine NTPPH. This cDNA sequence was searched against NCBI public EST, Pfizer proprietary (Pfizer, Groton Conn.), and Incyte LIFESEQ databases (Incyte Pharmaceuticals). The partial sequence failed to identify any homologous public ESTs; however, homologous sequences were found in three human chondrocyte libraries in the Pfizer database.

Incyte Clone 422069 was completely sequenced. Comparison of the deduced protein sequences from Incyte Clone 422069 and the partial porcine NTPPH revealed that the proteins were 90% identical at the amino acid level. Ligation reactions from the normal (SATPF010) and osteoarthritic (SATPF008) human chondrocyte libraries were electroporated into DH10B $E.\ coli$, and $1.1\times10^6$ independent cDNA clones were generated from each library.

SATPF008 was screened ($5\times10^6$ clones) with a 700 bp BamH1 fragment from the 5'-end of Incyte Clone 422069. After secondary and tertiary screening of the library, clones were characterized by partial sequence analysis and restriction mapping. Four independent clones were isolated that spanned the complete coding region for NTPPH-1.The 5'-half of the cDNA encoding NTPPH-1 was also generated by PCR amplification of the cDNA library using a NTPPH-1 -specific primer and a pINCY vector-specific primer. The resultant PCR product in combination with Y22069 predicted a full-length cDNA clone of 4.4 kb which agrees with the size of the mRNA identified by Northern hybridization. The 5' sequence of the PCR-generated cDNA corresponded to sequences from library-generated cDNA clones. The four library-derived cDNA clones s were sequenced and used to predict the amino acid sequence of NTPPH-1.

V Northern Analysis

Membrane-based northern analyses of human, dog and rabbit joint tissue RNA samples demonstrated the highest level of NTPPH-1 expression in articular cartilage and lower, but significant, expression in synovium, meniscus, tendon and ligament. Expression studies on additional human tissues demonstrated significant mRNA levels in skeletal muscle, heart muscle and bone marrow; and lower, but detectable, levels in trachea, spinal cord, thyroid, stomach, testis, uterus, small intestine, colon, thymus, placenta, lymph and adrenal tissue (cf. Sambrook et al., supra).

Computer techniques analogous to northern analysis were also performed using BLAST (Altschul (1993) supra, Altschul (1990) supra). The basis of the search is the product score which is defined as:

% sequence identity×% maximum BLAST score/100

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The sequence encoding NTPPH-1 was used to search for identical or related molecules in the NCBI and the LIFESEQ databases. This analysis showed NTPPH-1 homology with three human EST clones from skeletal muscle, ovary and heart (cf FIG. 2A) and with numerous Incyte Clones, many of which were from chondrocyte cDNA libraries and the remainder of which were dispersed among other tissues (FIG. 5).

VI Extension of NTPPH-1 Encoding Polynucleotides

The nucleic acid sequence encoding NTPPH-1 was used to design oligonucleotide primers for obtaining 5' regulatory sequences using an appropriate genomic library. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 software (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer—primer dimerizations was avoided.

Selected human cDNA libraries (GIBCO/BRL) were used to extend the sequence If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using a Peltier thermal cycler (PTC200; M.J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK (QIAGEN Inc., Chatsworth, Calif.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2–3 hours or overnight at 16° C. Competent E. coli cells (in 40 μl of appropriate media) were transformed with 3 μl of ligation mixture and cultured in 80 μl of SOC medium (Sambrook et al., supra). After incubation for one hour at 37° C., the E. coli mixture was plated on Luria Bertani (LB)-agar (Sambrook et al., supra) containing 2× Carb. The following day, several colonies were randomly picked from each plate and cultured in 150 μl of liquid LB/2× Carb medium placed in an individual well of an appropriate, commercially-available, sterile 96-well microtiter plate. The following day, 5 μl of each overnight culture was transferred into a non-sterile 96-well plate and after dilution 1:10 with water, 5 μl of each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

VII Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 μCi of [γ-$^{32}$P] adenosine triphosphate (Amersham) and T4 polynucleotide kinase (DuPont NEN, Boston, Mass.). The labeled oligonucleotides are substantially purified with SEPHADEX G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Kodak, Rochester, N.Y.) is exposed to the blots, or the a Phosphoimager cassette (Molecular Dynamics, Sunnyvale, Calif.), hybridization patterns are compared visually.

VIII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the microarray.

IX Complementary Polynucleotides

Sequence complementary to the NTPPH-1-encoding sequence, or any part thereof, is used to decrease or inhibit expression of naturally occurring NTPPH-1. Although use of oligonucleotides comprising from about 15 to about 30 base-pairs is described, essentially the same procedure is used with smaller or larger sequence fragments. Appropriate oligonucleotides are designed using OLIGO 4.06 software and the coding sequence of NTPPH-1, SEQ ID NO:1. To inhibit transcription, a complementary oligonucleotide is designed from the most unique 5' sequence and used to prevent promoter binding to the coding sequence. To inhibit translation, a complementary oligonucleotide is designed to prevent ribosomal binding to the NTPPH-1-encoding transcript.

X Expression of NTPPH-1

The cDNA encoding NTPPH-1 is used to express both full-length and truncated forms of recombinant NTPPH. Expression of NTPPI1 is accomplished by subcloning the cDNAs into appropriate vectors and transforming the vectors into host cells. In this case, the cloning vector was used to express NTPPH-1 in the baculovirus Fast-BAC system (GIBCO/BRL). Upstream of the cloning site, this vector contains a promoter for polyhedron coat protein. Infection of an insect cell line such as SF9 with the recombinant baculovirus results in the expression of NTPPH-1. Signal residues direct the secretion of NTPPH-1 into the culture media which can be used directly in the following assay for activity.

XI Demonstration of NTPPH-1 Activity

Human nucleotide pyrophosphohydrolase activity is analyzed using thymidine monophosphate paranitrophenyl ester or $^{32}$P gamma labeled ATP as substrate. Media are chromatographed and peak fractions are analyzed kinetically as described in Cardenal, A. et al. (1996; Arthritis Rheum. 39:252–256).

XII Production of NTPPH-1 Specific Antibodies

The amino acid sequence deduced from the cDNA encoding NTPPH-1 is analyzed using DNASTAR software (DNASTAR Inc.) to determine regions of high immunogenicity and a corresponding oligopeptide is synthesized and used to raise anti-NTPPH-1 antibodies. The selection of appropriate peptide sequences and the techniques for antibody production by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems 431A peptide synthesizer using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XIII Purification of Naturally Occurring NTPPH-1 Using Specific Antibodies

Naturally occurring or recombinant NTPPH-1 is substantially purified by immunoaffinity chromatography using antibodies specific for NTPPH-1. An immunoaffinity column is constructed by covalently coupling NTPPH-1 antibody to an activated chromatographic resin, such as CNBr-activated SEPHAROSE (Pharmacia & Upjohn). After the coupling, the resin is blocked and washed according to the manufacturer's instructions.

Media containing NTPPH-1 is passed over the immunoaffinity column, and the column is washed under conditions that allow the preferential absorbance of NTPPH-1 (e.g., high ionic strength buffers in the presence of detergent). The column is eluted under conditions that disrupt antibody/NTPPH-1 binding (eg, a buffer of pH 2–3 or a high concentration of a chaotrope, such as urea or thiocyanate ion), and NTPPH-1 is collected.

XIV Identification of Molecules Which Interact with NTPPH-1

NTPPH-1 or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled NTPPH-1, washed and any wells with labeled NTPPH-1 complex are assayed. Data obtained using different concentrations of NTPPH-1 are used to calculate values for the number, affinity, and association of NTPPH-1 with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A substantially purified human nucleotide pyrophosphohydrolase (NTPPH-1) consisting of the amino acid sequence of SEQ ID NO:1 or fragments thereof.

2. An isolated and purified polynucleotide sequence encoding the human NTPPH-1 of claim 1 or fragments of said polynucleotide sequence.

3. A composition comprising the polynucleotide sequence of claim 2.

4. A polynucleotide sequence which hybridizes under stringent wash conditions of 0.1× SSC and 0.05% SDS to the polynucleotide sequence of claim 2.

5. A polynucleotide sequence which is fully complementary to the polynucleotide sequence of claim 2 or fragments thereof.

6. An isolated and purified polynucleotide sequence of claim 2 comprising SEQ ID NO:2 or fragments thereof.

7. A polynucleotide sequence which is fully complementary to the polynucleotide sequence of claim 6.

8. An expression vector containing the polynucleotide sequence of claim 2 or an enzymatically active fragment thereof.

9. A host cell containing the vector of claim 8.

10. A method for producing a polypeptide consisting of the amino acid sequence of SEQ ID NO:1, or a fragment thereof, the method comprising the steps of:

a) culturing the host cell of claim 9 under conditions suitable for the expression of the polypeptide; and b) recovering the polypeptide from the host cell culture.

11. A pharmaceutical composition comprising a substantially purified human nucleotide pyrophosphohydrolase having the amino acid sequence of SEQ ID NO:1 in conjunction with a suitable pharmaceutical carrier.

12. A method for detecting a polynucleotide which encodes human NTPPH-1 in a biological sample comprising the steps of:

a) hybridizing the polynucleotide of claim 5 to nucleic acid material of a biological sample, thereby forming a hybridization complex; and b) detecting said hybridization complex, wherein the presence of said complex correlates with the presence of a polynucleotide encoding human NTPPH-1 in said biological sample.

13. The method of claim 12 wherein the nucleic acid material is amplified by the polymerase chain reaction prior to hybridization.

* * * * *